United States Patent [19]
Riviere et al.

[11] Patent Number: 6,066,091
[45] Date of Patent: May 23, 2000

[54] METHODS, SYSTEMS AND PRODUCTS FOR DETERMINING DRUG WITHDRAWAL INTERVALS

[75] Inventors: Jim E. Riviere, Raleigh; Tomás Martin-Jiménez; Ronald E. Baynes, both of Cary, all of N.C.; Arthur L. Craigmill, Oregon House, Calif.

[73] Assignee: North Carolina State University, Raleigh, N.C.

[21] Appl. No.: 09/027,670

[22] Filed: Feb. 23, 1998

[51] Int. Cl.$^7$ .................................................. A61N 5/00
[52] U.S. Cl. ............................ 600/300; 128/920; 128/898
[58] Field of Search ................................. 600/300, 301; 128/920

[56] References Cited

U.S. PATENT DOCUMENTS

5,660,995  8/1997  O'Connor .............................. 435/7.93

OTHER PUBLICATIONS

J. Riviere; Pharmacologic principles of residue avoidance for veterinary practitioners; JAVMA 198:809–815 (1991).

D. Concordet et al.; The withdrawal time estimation of veterinary drugs revisited; *J. Vet. Pharmacol. Therap.* 20:380–386 (1997).

R. Ellis; Codex Committee on Residues of Veterinary Drugs in Foods Status Report 1996.

W. Moats et al.; Veterinary Drug Residues Food Safety 1995.

S. Fitzpatrick et al.; Dietary intake estimates as a means to the harmonization of maximum residue levels for veterinary drugs. I. Concept; *J. Vet. Pharmacol. Therap.* 18:325–327 (1995).

G. Guest et al.; Estimating the Dietary Intake of Veterinary Drug Residues.

S. Fitzpartrick et al.; Dietary Intake Estimates as a Means to the Harmonization of Maximum Residue Levels for Veterinary Drugs; *Regulatory Toxicology and Pharmacology* 24:177–183 (1996).

J. Riviere et al.; Chemical Residues in Tissues of Food Animals; 1148–1157.

N. Weber; Residue Concerns for Land–Based Animal Derived Food; *Dairy, Food and Environmental Sanitation* 12, No. 3:144–148 (1992).

J. Paige et al.; Public Health Impact on Drug Residues in Animal Tissues; *Vet Human Toxicol* 39(3):162169 (1997).

General Principles for Evaluating the Safety of Compounds used in Food–Producing Animals; *U.S. Dept. of Health and Human Services* (Revised Jul. 1994).

*Primary Examiner*—Robert L. Nasser
*Assistant Examiner*—Michael Astorino
*Attorney, Agent, or Firm*—Myers Bigel Sibley & Sajovec

[57] ABSTRACT

A first aspect of the invention is a method of estimating a withdrawal interval for an adjusted dose of a compound from a prior withdrawal time for a corresponding prior dose of that compound, corresponding half-life data and a tolerance concentration, for a tissue of interest. The method comprises selecting an adjusted dose for the compound for which a withdrawal interval is to be determined, and extrapolating a withdrawal interval from (a) the prior dose, (b) the prior withdrawal time, (c) the half-life data, and (d) the tolerance concentration. The process is useful for determining a withdrawal interval for an extralabel (i.e., non-approved) use of a drug in the same or a different jurisdiction for which a previous use has been approved, and can be used to determine an appropriate withdrawl interval for a drug in food products exported from one jurisdiction to another. Data processing systems and computer program products for carrying out the foregoing are also disclosed.

34 Claims, 11 Drawing Sheets

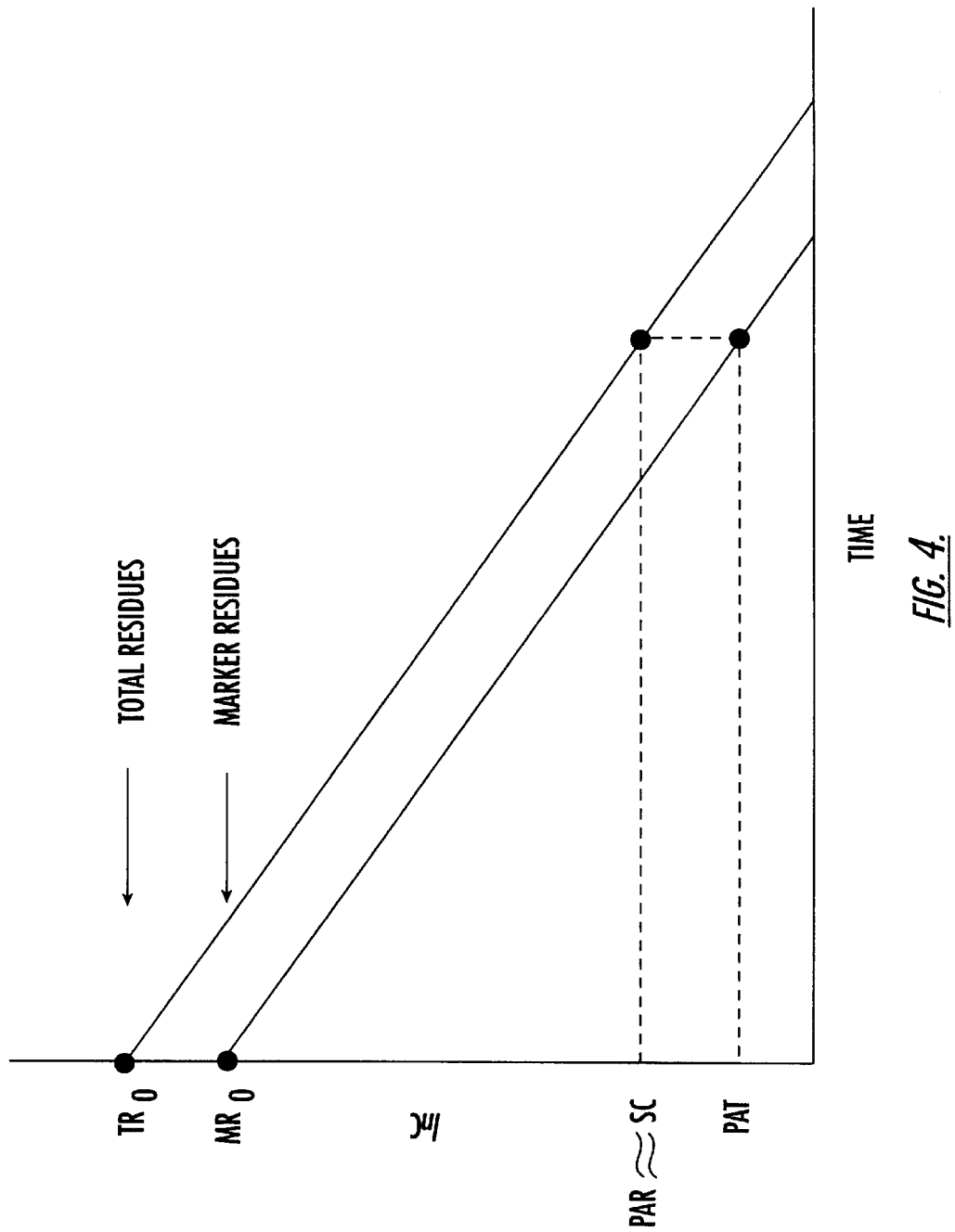

METHODS, SYSTEMS AND PRODUCTS FOR DETERMINING DRUG WITHDRAWAL INTERVALS

This invention was made with Government support under Grant No. 97-EFSQ-1-0099 from the United States Department of Agriculture in support of the Food Animal Residue Avoidance Databank (FARAD) program. The Government has certain rights to this invention.

FIELD OF THE INVENTION

This invention relates to methods and apparatus for determining a withdrawal interval for a new or off-label dosage of a compound, for consumable products derived from farm animals.

BACKGROUND OF THE INVENTION

Food safety is an important public health issue. One aspect of food safety is insuring that residue concentrations of drugs and other compounds in consumable products derived from food animals are at, or below, levels that are acceptable for human consumption. Programs for insuring such requirements are met are administered by various government regulatory agencies such as (in the United States) the Food and Drug Administration (FDA) and the United States Department of Agriculture (USDA).

In general, veterinary pharmaceutical products must meet standards of safety and efficacy, in much the same manner as human pharmaceutical products. In addition, it must be assured that an adequate time elapses between treatment of an animal and the harvesting of consumable products from that animal. Such times are termed "withdrawal times". From factors such as an acceptable daily intake of a given compound for human consumption, certain assumptions on the composition of the diet of a given population, maximum residual levels (MRL; referred to as tolerance level in the United States) for various compounds in food products are determined. The withdrawal time is an indication of the time required, after treatment by or exposure to a particular compound, for the concentration of a compound (or byproduct of that compound) to reduce to a level at or below the tolerance in the tissue of interest (e.g., milk, meat). Once the withdrawal interval has elapsed, the tissue of interest can be harvested and used for human consumption. Food products are monitored for compliance with such tolerances, and the detection of levels in excess of acceptable tolerances can result in legal penalties.

Withdrawal intervals are currently determined empirically: a group of animals is administered a known drug at the dosage for which approval is sought, and animals within that group are sacrificed over time and the amount of the drug or residue measured in the tissue of interest. The withdrawal time is determined from the pharmacological data so obtained. A problem with this approach is that such studies require utilization of large groups of animals. An additional problem is that the study must be repeated, with an additional group of animals, when a new dosage is contemplated.

Veterinary and humane considerations can weigh in favor of using an approved drug for a sick animal at a dosage for which a withdrawal time is not known. In cases like this, either a best guess of a withdrawal time must be made, or an animal study must be conducted. If an insufficient withdrawal time is used and unacceptably high levels of the drug are detected in tissue derived from the treated animal, then legal liability under applicable food safety statutes may nevertheless attach.

Accordingly, there is a need for new techniques for determining withdrawal intervals in food animals.

SUMMARY OF THE INVENTION

A first aspect of the invention is a method of estimating a withdrawal interval for an adjusted dose of a compound from a prior withdrawal time for a corresponding prior dose of that compound, corresponding half-life data and a tolerance concentration, for a tissue of interest. The method comprises selecting an adjusted dose for the compound for which a withdrawal interval is to be determined, and extrapolating a withdrawal interval from (a) the prior dose, (b) the prior withdrawal time, (c) the half-life data, and (d) the tolerance concentration. An animal subject may then be administered the adjusted dosage of the compound, and then euthanized after the indicated withdrawal interval is completed and the tissue of interest harvested. Where the dose is administered prior to the extrapolating step (as may be the case with environmental contaminants consumed by food animals) the animal is euthanized and the tissue of interest harvested after the withdrawal interval from the date of administration of the compound has been completed.

In general, and as explained in greater detail below, the extrapolating step is carried out based on the slope of the line representing the tissue depletion for the compound in the tissue at the prior dose corresponding to the slope of the line representing the virtual depletion of the $99^{th}$ percentile of the population of depleting animals for the compound in the tissue at the adjusted dose. Stated differently, the extrapolating step is carried out based on the depletion rate constant for the compound in the tissue at the prior dose corresponding to the virtual depletion rate constant representing the virtual depletion of the $99^{th}$ percentile of the population of depleting animals for the compound in the tissue at the adjusted dose.

In carrying out the foregoing method, any of a variety of half-life data may be employed. The half-life data may be empirically determined data, such as an empirically determined effective residue half-life. The half-life data may be model pharmacokinetic data or an assumed or predetermined half-life multiplier. The tolerance concentration may be an official Tolerance (Tol) as determined by United States regulatory law, or may be a Maximum Residue Level (MRL) as determined by the laws of other jurisdictions. Where an MRL or Tol for one jurisdiction is used to determine a withdrawal interval for another jurisdiction in which a Tol or MRL has not been set, a provisional acceptable residue (PAR) or provisional acceptable tolerance (PAT) may be determined and used as the tolerance concentration in the foregoing, as explained in greater detail below.

When the half-life data is an empirically determined effective residue half-life, the step of extrapolating a withdrawal interval may be carried out by: determining a half-life multiplier from the first withdrawal time and the residue half-life; determining a concentration at time zero for the first dose from the tolerance concentration and the half-life multiplier; determining a concentration at time zero for the second dose from the first dose, the second dose, and the concentration at time zero for the first dose; and then calculating the withdrawal interval from (a) the residue half-life, (b) the concentration at time zero for the second dose, and (c) the tolerance concentration. The calculating step may comprise executing the formula:

$$WDI = ERH \times Ln(C^{**}/TOL) \times 1.44$$

wherein: WDI=withdrawal interval; ERH=effective residue half-life; $C^{**}$=concentration at time zero for the second dose; and TOL=tolerance concentration.

When the half-life data is a half-life multiplier, the step of extrapolating a withdrawal interval may be carried out by: determining a residue half life from the first withdrawal time and the predetermined half-life multiplier; determining a concentration at time zero for the first dose from the tolerance concentration and the predetermined half-life multiplier; determining a concentration at time zero for the second dose from the first dose, the second dose, and the concentration at time zero for the first dose; and then calculating the withdrawal interval from (a) the residue half-life, (b) the concentration at time zero for the second dose, and (c) the tolerance concentration. The calculating step may comprise executing the formula:

$$WDI = ERH \times Ln(C^{**}/TOL) \times 1.44$$

wherein: WDI=withdrawal interval; ERH=effective residue half-life; $C^{**}$=concentration at time zero for the second dose; and TOL=tolerance concentration. The half life multiplier may be any suitable multiplier, e.g., a number from 1 to 10, and in one embodiment is 5.

The tolerance concentration may be a provisional acceptable residue (PAR) determined by the method comprising: providing an acceptable daily intake for the compound; partitioning the acceptable daily intake among tissues according to a set of partitioning instructions; and deriving the provisional acceptable residue for the tissue of interest from the partitioned acceptable daily intake.

When the compound is monitored in the tissue by monitoring a marker residue (i.e., one or more detectable compounds), the tolerance concentration may be a provisional acceptable tolerance (PAT) determined by the method comprising: providing an acceptable daily intake for the compound; partitioning the acceptable daily intake among tissues according to a set of partitioning instructions; deriving the provisional acceptable residue for the tissue of interest from the partitioned acceptable daily intake; and determining a provisional acceptable tolerance from the provisional acceptable residue.

When the prior dose and the adjusted dose are carried out under different conditions (e.g., different formulations and/or different routes of administration), the extrapolating step may be preceded by the step of normalizing the conditions of the prior dose to the conditions of the adjusted dose.

In addition, the adjusted dose may be modified from the prior dose to account for species differences, disease differences, or both. The adjusted dose may be modified for disease differences including a change in clearance, a change in volume of distribution, and combinations thereof. This may be carried out based on known kinetic data. The adjusted dose may be modified for species differences based on known allometric data.

A second aspect of the present invention is a data processing system that carries out the foregoing methods.

A third aspect of the present invention is a computer program product for carrying out the foregoing methods and implementing the foregoing systems.

The foregoing and other objects and aspects of the present invention are explained in detail in the drawings herein and the specification set forth below, in which:

BRIEF DESCRIPTION OF THE DRAWINGS

FIG. 4 is a graphical illustration of the conversion of a provisional acceptable residue to a provisional acceptable tolerance (PAT).

DETAILED DESCRIPTION OF THE PREFERRED EMBODIMENTS

Figure 1:
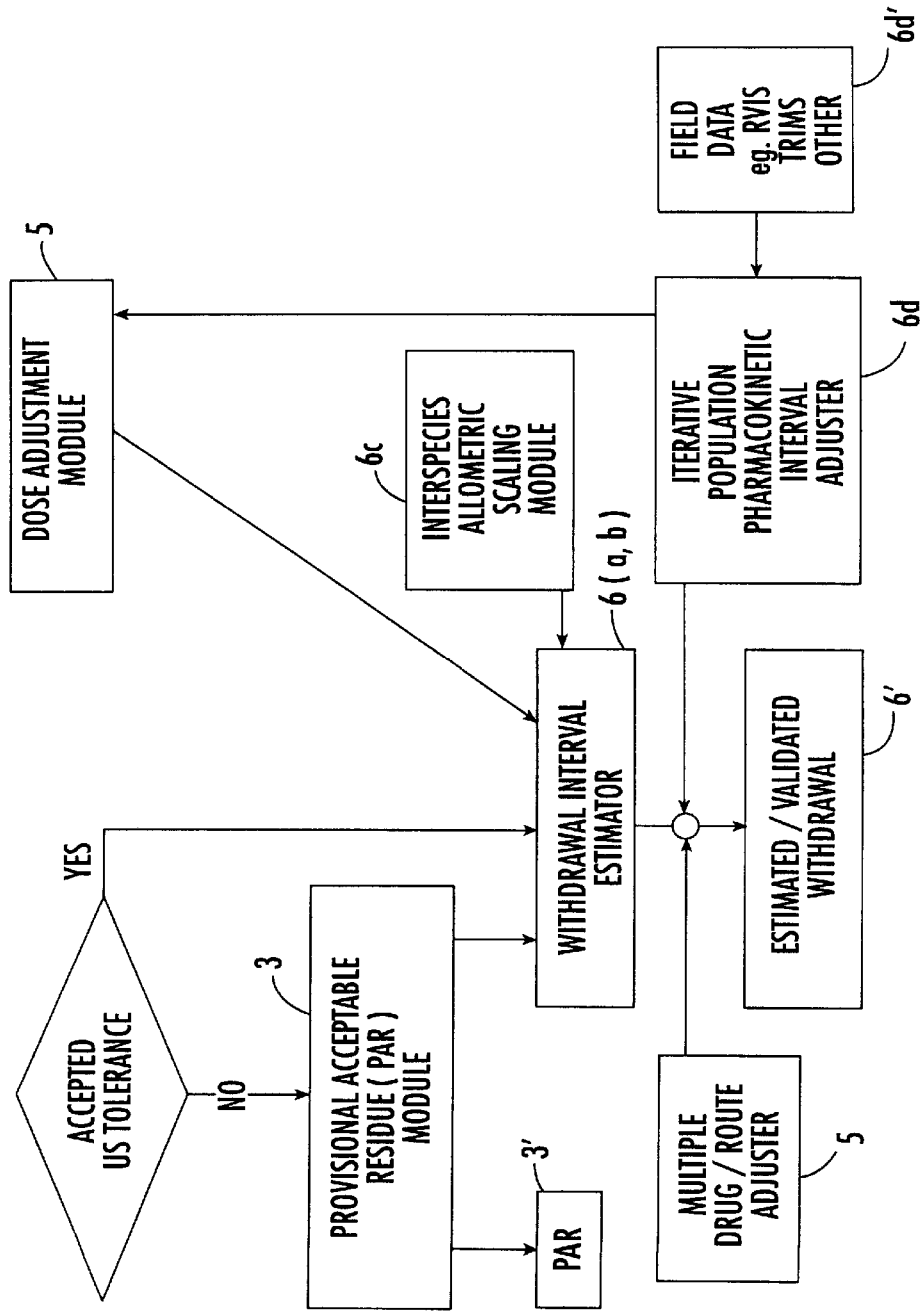
FIG. 1 schematically illustrates an extrapolated withdrawal interval estimator system according to a preferred embodiment of the present invention.

This invention may be embodied in many different forms and should not be construed as limiting to the embodiments set forth herein. Rather, these embodiments are provided so that this disclosure will be thorough and complete, and will fully convey the scope of the invention to those skilled in the art.

It will be understood that elements of the invention can be implemented by general and/or special purpose hardware-based system that perform the specified functions or steps, or by combinations of general and/or special purpose hardware and software instructions.

These program instructions may be provided to a processor to produce a machine, such that the instructions that execute on the processor create means for implementing the functions specified in the illustrations. The computer program instructions may be executed by a processor to cause a series of operational steps to be performed by the processor to produce a computer implemented process such that the instructions which execute on the processor provide steps for implementing the functions specified in the illustrations. Keyboards, touch-screens, mouse/screen pointer combinations and the like all provide means for accepting selection of a particular parameter by the systems described herein. Accordingly, the figures herein support combinations of means for performing the specified functions, combinations of steps for performing the specified functions and program instruction means for performing the specified functions.

The following terms and abbreviations are used herein. Some of these terms (and other terms used herein) are in accordance with standard regulatory usage by the applicable regulatory agency (e.g., the United States Department of Agriculture (USDA); the United States Food and Drug Administration (FDA); and the counterpart regulatory agencies of other jurisdictions); others are defined herein for the purpose of explaining and carrying out the instant invention:

ADI: Acceptable Daily Intake (typically expressed as mg or ug of compound/60kg person/day). Obtainable from U.S.

or foreign data files. Generally, the ADI is calculated by dividing the NOEL obtained in the toxicology study with the most appropriate species by a safety factor.

C*: Estimated (typically determined at the $99^{th}$ percentile) $C_T$ for label dose.

C**: Estimated (typically determined at the $99^{th}$ percentile) $C_T$ for extralabel dose.

CF: Correction Factor to adjust half-life label-dose for disease or altered physiology of extralabel conditions.

$C_T$: Mean concentration in tissue at time zero which reflects the administered working label dose.

E_Dose: Extralabel dose.

ERH: Effective Residue Half-Life. The half-life related to the slope of the virtual line which defines the upper bound of the applicable confidence interval (typically the upper bound of a 95% confidence interval around the $99^{th}$ percentile) for ETH (operationally defined as the line connecting $WDT_{99}$ and C*).

ETH: Effective Tissue Half-life. Mean ($50^{th}$ percentile) tissue depletion half life.

EW_Dose: Extra-label Working Dose. Normalized by dosage regimen.

EWE: Extrapolated Withdrawal-interval Estimator algorithm.

Hlife: Half-Life.

HLM: Half-Life Multiplier. Number of half-lives to reach tolerance/MRL level.

IPPIA: Iterative Population Pharmacokinetics Interval Adjuster.

L-Dose: Label-Dose.

LOQ: Limit of Quantitation. The lowest concentration that can be reproducibly detected by an analytical method. The LOQ is the Tol/MRL in some jurisdictions that have "zero-residue" policies in effect.

LW_Dose: Label Working Dose. Normalized by dosage regimen.

MRL: Maximum Residue Levels (typically expressed as mg/kg). This is similar to tolerance derivation in the U.S.

Marker residue: The compound, degredation product(s) of that compound, or combination thereof in a tissue tissue used to determine the withdrawal time for that tissue for the compound administered to the animal, and from which the marker residue is derived.

NOEL: The no observed effect level. Defined as the greatest concentration or amount of an agent, found by study or observation, that causes no detectable, usually adverse, alteration of morphology, functional capacity, growth, development or lifespan of the target (e.g., the subject of a toxicology study).

PARs: Provisional Acceptable Residues (typically expressed as ppm). Derivation of PARs is similar to FDA-CVM derivation of SC as defined below.

PATs: Provisional acceptable tolerances (typically expressed as ppm). Derivation of PATs is similar to FDA-CVM derivation of tolerance as defined below.

RVIS: Residue Violation Information System. USDA regulatory residue violation database.

SC: Safe Concentration (typically expressed as ppm). The concentration of residues in tissues considered safe for human consumption. One definition of SC is as follows:

$$SC = \frac{ADI(mg/kg/day) \times 60 \text{ kg}}{\text{grams consumed/day}}$$

TOL: Tolerance level (typically expressed as either ppm or ppb). The concentration of the marker residue in the target tissue when the concentration of the total residue of toxicological concern is equal to the permitted safe concentration in the last tissue to deplete to its safe concentration.

TRIMS: Tissue Residue Information Management System. FDA monitoring residue database.

WDI: Withdrawal Interval. The EWE estimated withdrawal period. Defined to avoid confusion with WDT.

WDT: The approved label-dose Withdrawal time, as approved by the appropriate regulatory agency. Withdrawal time for FDA approved or foreign approved drugs.

The present invention may be employed with any farm, or food, animal, including but not limited to mammalian avian and aquatic (e.g., fish, crustacean) species such as cows, pigs, lamb, rabbit, chicken, turkey, ostrich, catfish, tilapia, trout, catfish, Mahi-Mahi, crayfish, shrimp, lobster, etc. Thus, examples of tissues that may be employed in the present invention include but are not limited to muscle (or meat), liver, kidney, fat, egg, and milk.

The present invention may be employed with any of a variety of compounds, including drugs, pesticides, and environmental contaminants, which may be administered to animals intentionally or unintentionally by any route of administration including, but not limited to, topical application to the skin or hide, inhalation, oral administration (e.g., a drug tablet, powder, granules or capsule; by the eating of food contaminated with a pesticide or environmental contaminant), parenteral injection (e.g., subcutaneous injection, intraperitoneal injection; intravenous injection). Illustrative examples of compounds that may be employed in connection with the present invention include, but are not limited to:

ampicillin, amoxacillin, fenthion, famphur, phosmet, chlorpyrifos, flunixin meglumine, trichlorofon, doxycycline, lindane, methoxychlor, permethrin, acepromazine, detomidine, ketamine, xylazine, yohimbine, aspirin, dipyrone, ketoprofen, phenylbutazone, cephapirin, penicillin G, novobiocin, cloxacillin, erythromycin, tylosin, florfenicol, pyrantel, ciprofloxacin, doramectin, enrofloxacin, milbemycin oxime, danofloxacin, sarafloxacin, abamectin, albenzadole, azaperone, benzylpenicillin, carazolol, carbadox, ceftiofur sodium, chlortetracycline, oxytetracycline and tetracycline, clenbuterol, closantel, cypermethrin, alpha-cypermethrin, dexamethasone, diclazuril, dihydrostreptomycin and streptomycin, diminazene, doramectin, estradiol-17beta, febantel, fenbendazole, oxyfendazole, flubendazole, gentamicin, isometamidium ivermectin, levamisole, moxidectin neomicin, oxfendazole, progesterone, spectinomycin, spiramycin, all sulfonamides (e.g., sulfadimidine), streptomycin, testosterone, thiamphenicol, thiabendazole, tilmicosin, trenbolone acetate, triclabendazole, zeranol, etc. In general, many compounds that are used in the present invention have first order clearance kinetics in the tissue of interest Drugs and compounds may be administered to the animal by any route, including but not limited to topical, oral, parenteral (including intramuscular, intraveneous, intraarterial, subcutaneous, and intraperitoneal injection), transdermal, rectal, nasal, inhalation, etc.

One embodiment of the present invention is an extrapolated withdrawal-interval estimator (EWE), schematically illustrated in FIG. 1. This embodiment estimates a withdrawal interval (WDI) for an extralabel use of drugs in the United States. This process is consistent with US food safety standards and with the policies of extralabel drug use expounded in the AMDUCA regulations promulgated by FDA in 1997. It will be appreciated that the same process can be used to estimate an extralabel use of a drug in a jursdiction other than the United States, or to predict an appropriate WDI for use of a drug approved in one jurisdiction (e.g., a US drug) for export to another jurisdiction to meet the latter's food safety standards.

In overview, the process and apparatus of FIG. 1 obtains its data from two primary sources of information: the approved labeled reference product and pharmacokinetic data. In brief overview, the withdrawal interval estimator 6 (which may be either embodiment 6a or 6b below) receives a provisional acceptable residue, or PAR, from the PAR module (see blocks 3, 3'). Where the dose or route of administration differs between the approved dose and the extralabel dose a dose adjustment module 5 may be employed to normalize dosage, and where species is changed from approved dose to extralabel dose an interspecies allometric scaling module 6c may be employed to normalize data. As field data for the new dosage is accumulated, the estimate may be modified by the use of the iterative population pharmacokinetic interval adjuster module (see blocks 6d, 6d').

Figure 2:
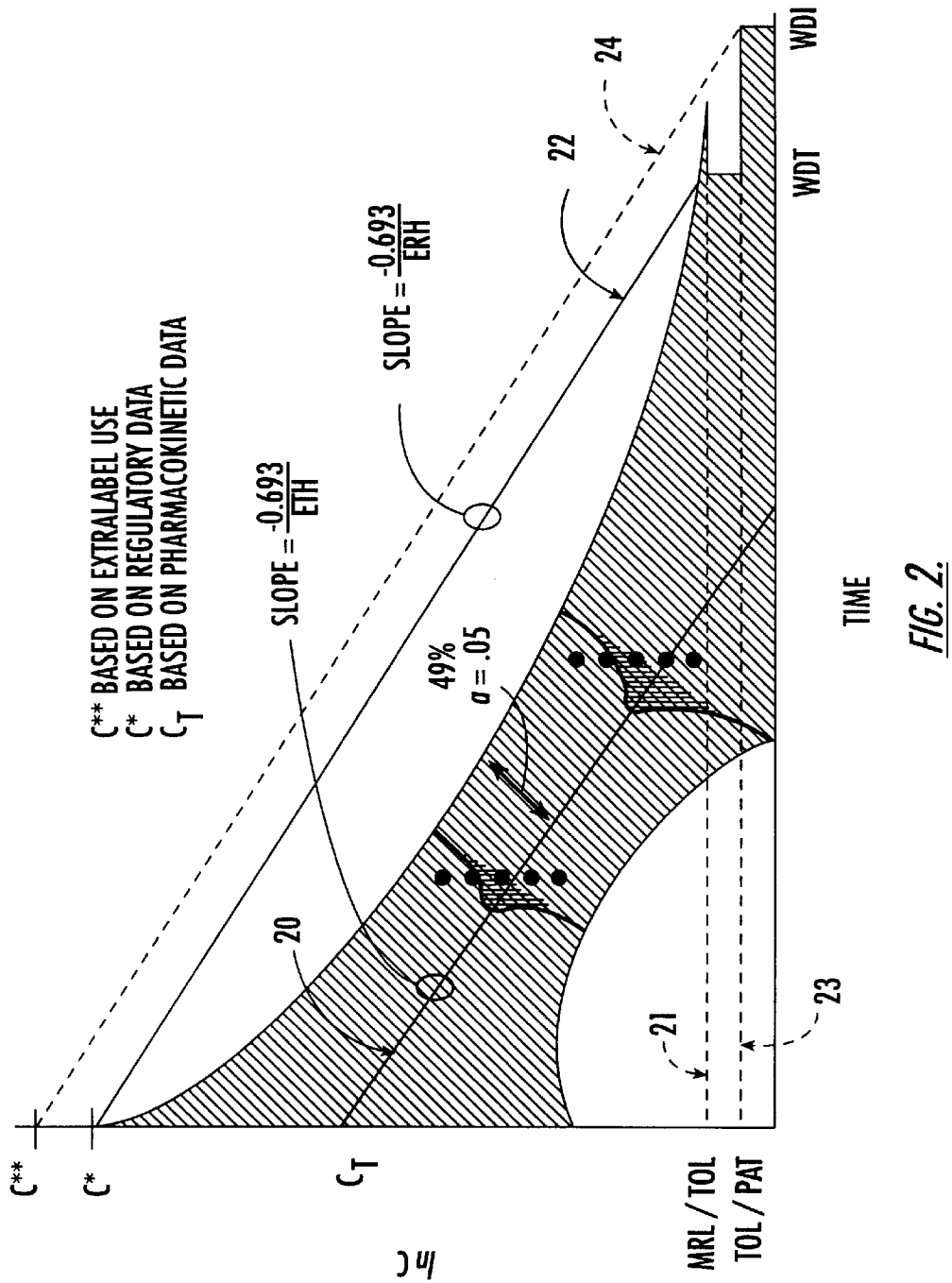
FIG. 2 illustrates example tissue depletion curves employed in carrying out a preferred embodiment of the present invention.

As shown in FIG. 2, a primary assumption in the present invention is that the label reference product contains a withdrawal time that statistically insures with 95% confidence that approximately 99% of the population of animals treated with this product under label dosage conditions will have tissue concentrations at slaughter below the established tolerances or maximum residue levels (MRLS; line 21) established as safe for that country. Thus any data extracted from this information is in reality an estimate of the upper band of the confidence interval for depletion (C*; line 22) in the worst case scenario in the rate limiting tissue (defined either as having the slowest depletion or as most sensitive from a food safety perspective).

Note that a confidence interval higher or lower than 95% can be used (e.g., a confidence interval of 90, 95, or 99 percent or more) and that a population percentile higher or lower than 99% can be employed (e.g., a percentile of 90, 95, 99, or 99.5 percent or more). In general, different parameters will still yield a line as in FIG. 2 having essentially the same slope, or will yield essentially the same depletion rate constant. Accordingly, it will be appreciated that it is the slope or rate constant that is significant to the operation of the instant invention, and not the assignment of a particular percentile or confidence interval.

Figure 3:
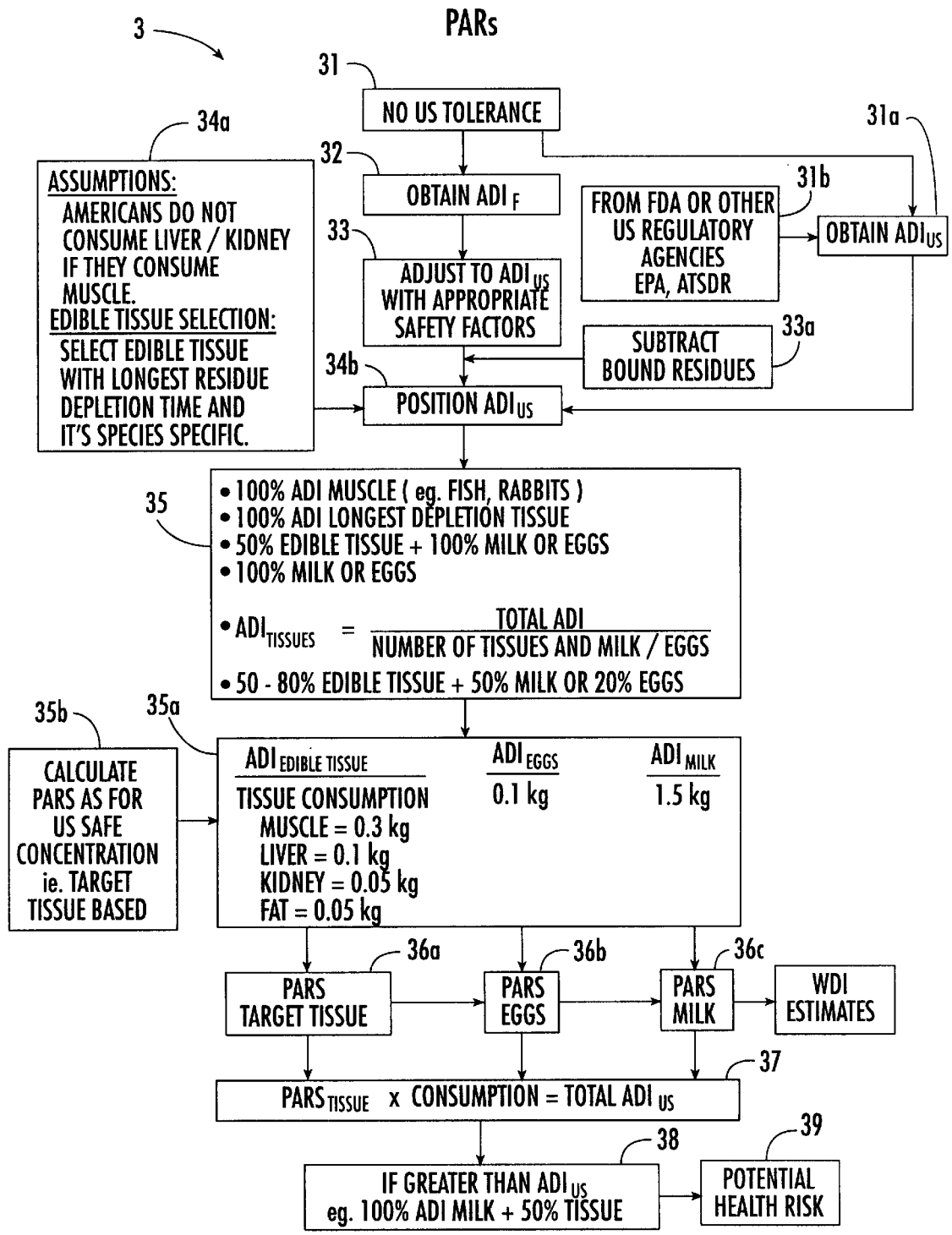
FIG. 3 illustrates a system for determining a provisional acceptable residue (PAR) in accordance with a preferred embodiment of the present invention.

Turning to FIG. 3, since, in the present example, the drug is to be used in the United States, when US approved labels are not available, data from other jurisdictions are the best source of information for food safety available. However, the foreign withdrawal time obtained from the label may not be appropriate for application in the United States, since different factors are used to extrapolate toxicology results (e.g. NOAELs) to estimates of human safety (e.g. Acceptable Daily Intake—ADI). However, it is assumed that foreign ADIs are the best available source of safety information which would be appropriate for US standards if the ADI were adjusted for US/foreign differences in safety factors and tissue-specific food consumption factors (see blocks 31, 32). Thus the EWE method and apparatus illustrated in FIG. 1 takes foreign ADIs and in the PARs module (schematically illustrated in FIG. 3), uses US assumptions procedures to partition the ADI over target tissues in accordance with partitioning instructions (FIG. 3, blocks 33, 33a, 34, 34a, 35, 35a, 35b) to arrive at PARs for each tissue (see blocks 36a, 36b, 36c, 36d). If US tolerances or safe levels are available, this step is not necessary (see blocks 31a, 31b). This step is also necessary for extralabel use in minor species and in this case would be applied using US ADIs as the input data. Finally, the PARs is further adjusted by a consumption factor since it is a safety parameter reflecting total residues, and compared against the original $ADI_{US}$ to identify potential health risks (blocks 37, 38, 39).

In some cases one or more marker residues are monitored rather than the drug or compound administered. As graphically illustrated in FIG. 4, the PAR is adjusted to the marker residue, which is monitored, and a Provisional Acceptable Tolerance (PAT) is calculated for each tissue to be used as the target concentration against which a WDI is determined.

Figure 5A:
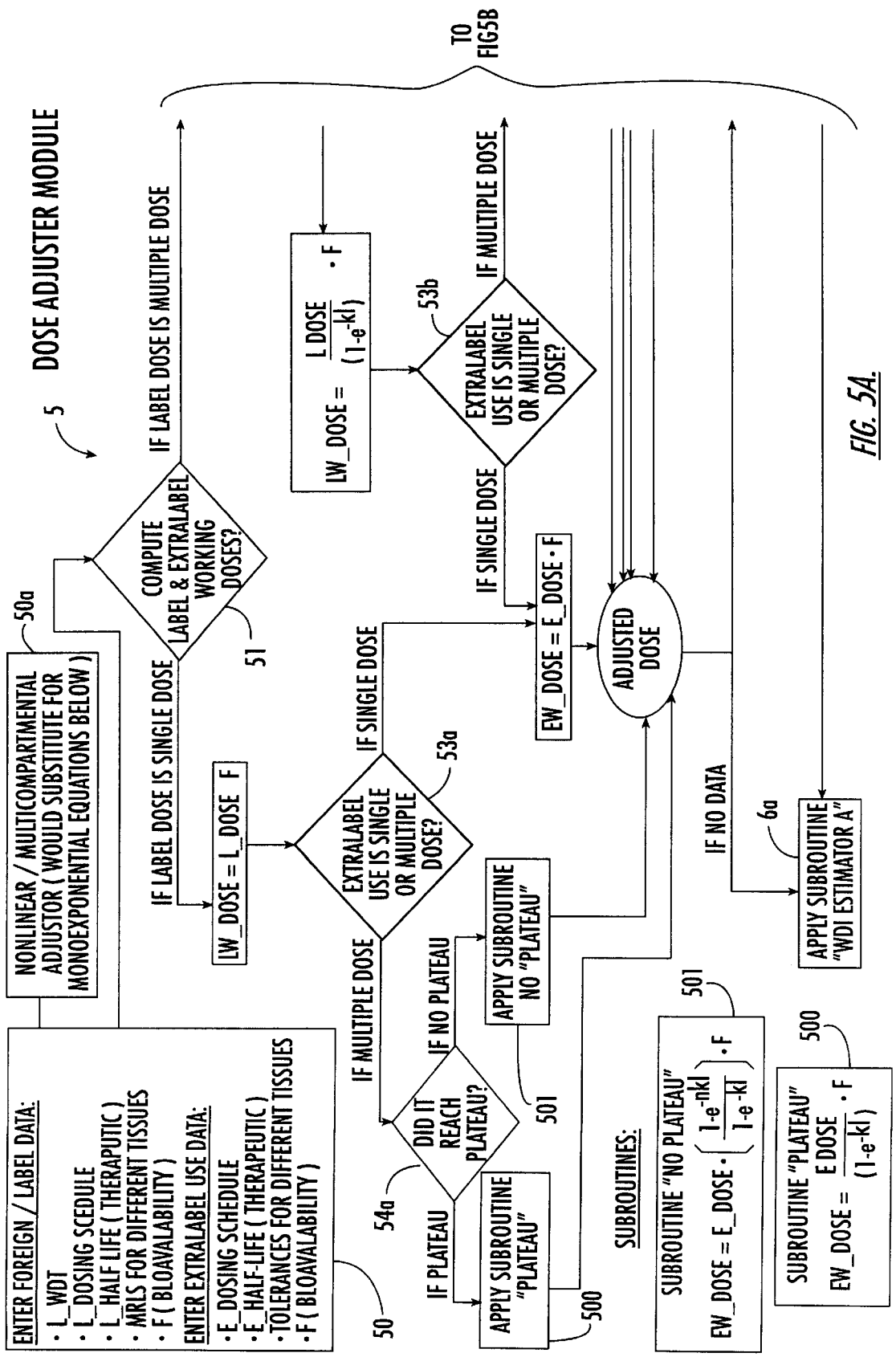
FIG. 5 illustrates operations performed by a dose adjuster system of a preferred embodiment of the present invention.
Figure 5B:
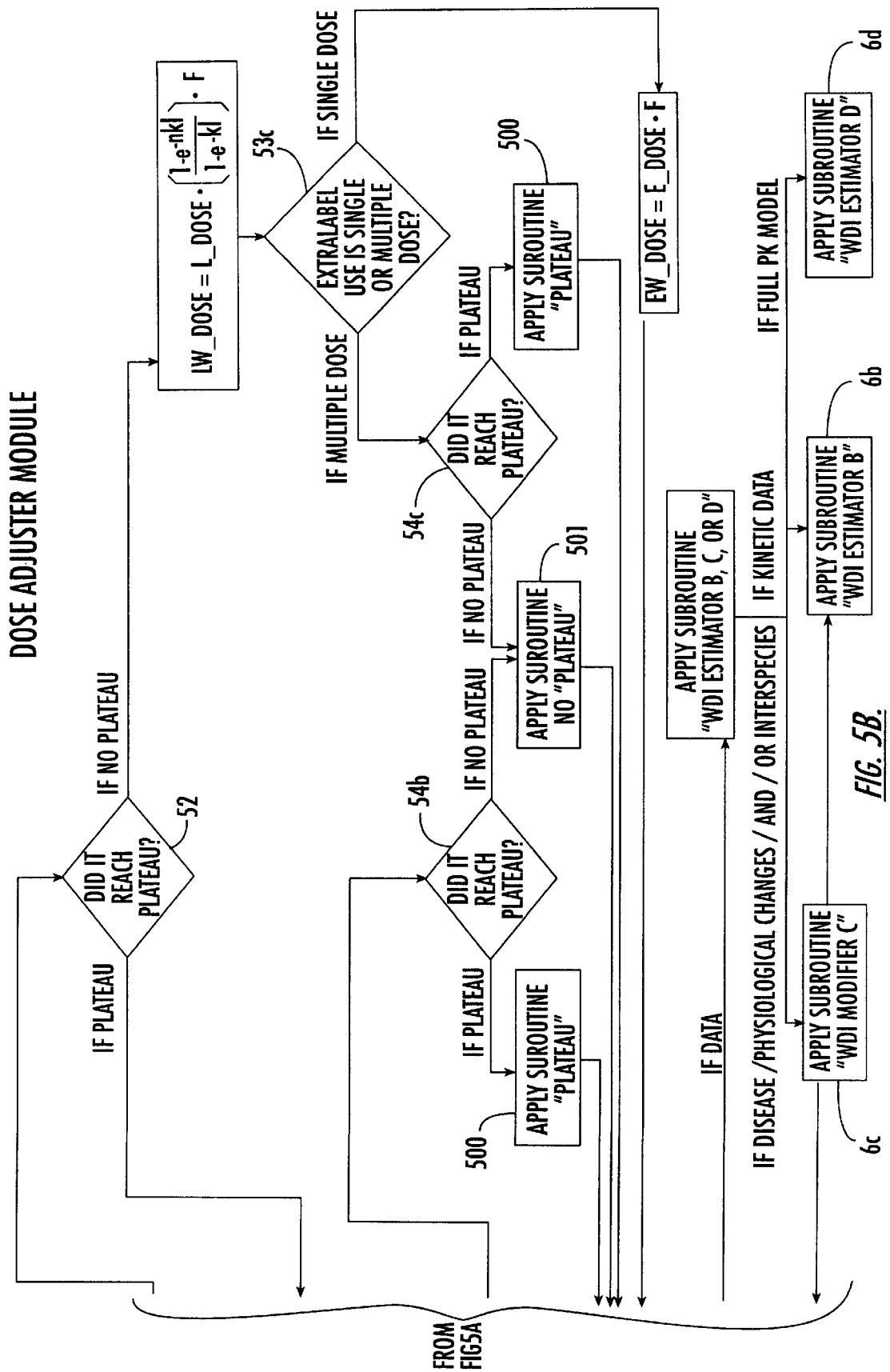

FIG. 5 illustrates the dose adjuster module (block 5 of FIG. 1) from data entry (block 50) to application of the WDI estimator or modifier routines (blocks 6a, 6b, 6c, 6d). This module normalizes label dosage to extralabel conditions by calculating working doses which reflect the amount of drug in the body at the time of the last drug administration. This is achieved by defining working doses (which normalizes or reflects the normalized amount of drug in the tissue at the end of a dosage regimen) for both the label {LW_Dose} and extralabel {EW_Dose} dosage conditions. The drug formulations selected to compare will have similar dosage formulations (e.g. rapid acting, long-acting) to insure that the rate limiting kinetic process is similar in both cases (e.g. systemic clearance versus absorption limited disposition). For example, if both label and extralabel usage are single doses, then the adjustment is simply based on a ratio of doses. However, if the label dose is multiple and the extralabel dose single, then standard clinical pharmacokinetic techniques are used to estimate working doses (blocks 51, 52, 53a, 53b, 53c, 54a, 54b, 54c, 500, 501).

In the FIG. 5, equations based on monoexponential disposition (steady state and non-steady state) are used, although if more precise multi-exponential or nonlinear models are available to describe tissue-sequestered or metabolized drugs, then they could be incorporated (block 50a). Similarly, differences in bioavailability (F) are allowed for and used if good information is available. If not, then F is set to 1.0 which is a conservative assumption from a food safety perspective. The result of this module are LW_Dose and EW_Dose, the latter being used to calculate the WDI.

The Withdrawal Interval Estimator 6 is a central feature of the EWE illustrated in FIG. 1. At this point, one has an EW_Dose and a target tissue concentration (MRL, Tol or PAT). The problem now is to use the label dose information to extract disposition parameters that reflect a level of statistical confidence appropriate to regulatory policies. To mathematically define a tissue depletion profile, two attributes are required: a slope reflecting rate of tissue decay, and an intercept reflecting drug concentration at some defined time. The regulatory data provides the latter in terms of the target tolerance, or MRL, which occurs for the entire population at the withdrawal time. However, the label working dose also gives similar information if the volume of distribution and/or plasma to tissue ratio is known. It must be stressed that this phase of the analysis is using the reference label data only to extract this depletion information and is not being used for any food safety extrapolations since other factors not applicable to the US regulatory environment (e.g. Good Veterinary Practices used in Europe) may modify the MRL relative to ADI-criteria alone. The assumption is that the statistics governing the establishment of an approved withdrawal time will insure that any parameters extrapolated from regulatory data will have a conservative statistical estimate built in. The overall strategy is outlined in FIG. 2, taken together with the various embodiments of the withdrawal interval estimators and modifier exemplified by FIGS. 6A, 6B, 6C, and 6D.

FIG. 2 defines two sets of intercepts and slope-parameters. Any parameter obtained from the literature (e.g. pharmacokinetic) or from raw data in regulatory submissions, is defined as representing mean population estimates ($50^{th}$ percentile). The zero-time intercept is thus $C_T$ and the slope of line 20 is $-0.693$/ETH, where ETH is the Effective Tissue Half-life. Since most tissue depletion data is governed by first-order pharmacokinetic decay, the concept of half-life is operative; otherwise, another model is used (see below).

Figure 6A:
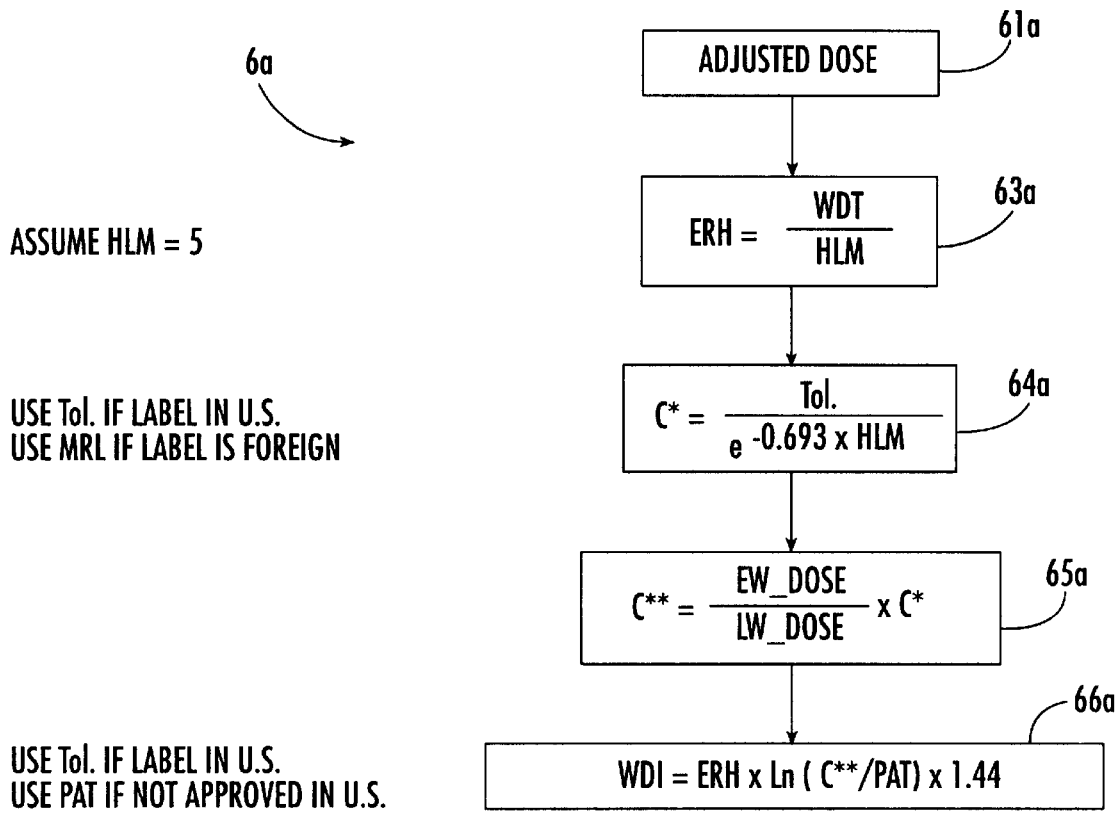
FIG. 6A illustrates operations performed by a first withdrawal interval estimator of one embodiment of the present invention, employed when kinetic/regulatory data are not available.
Figure 6B:
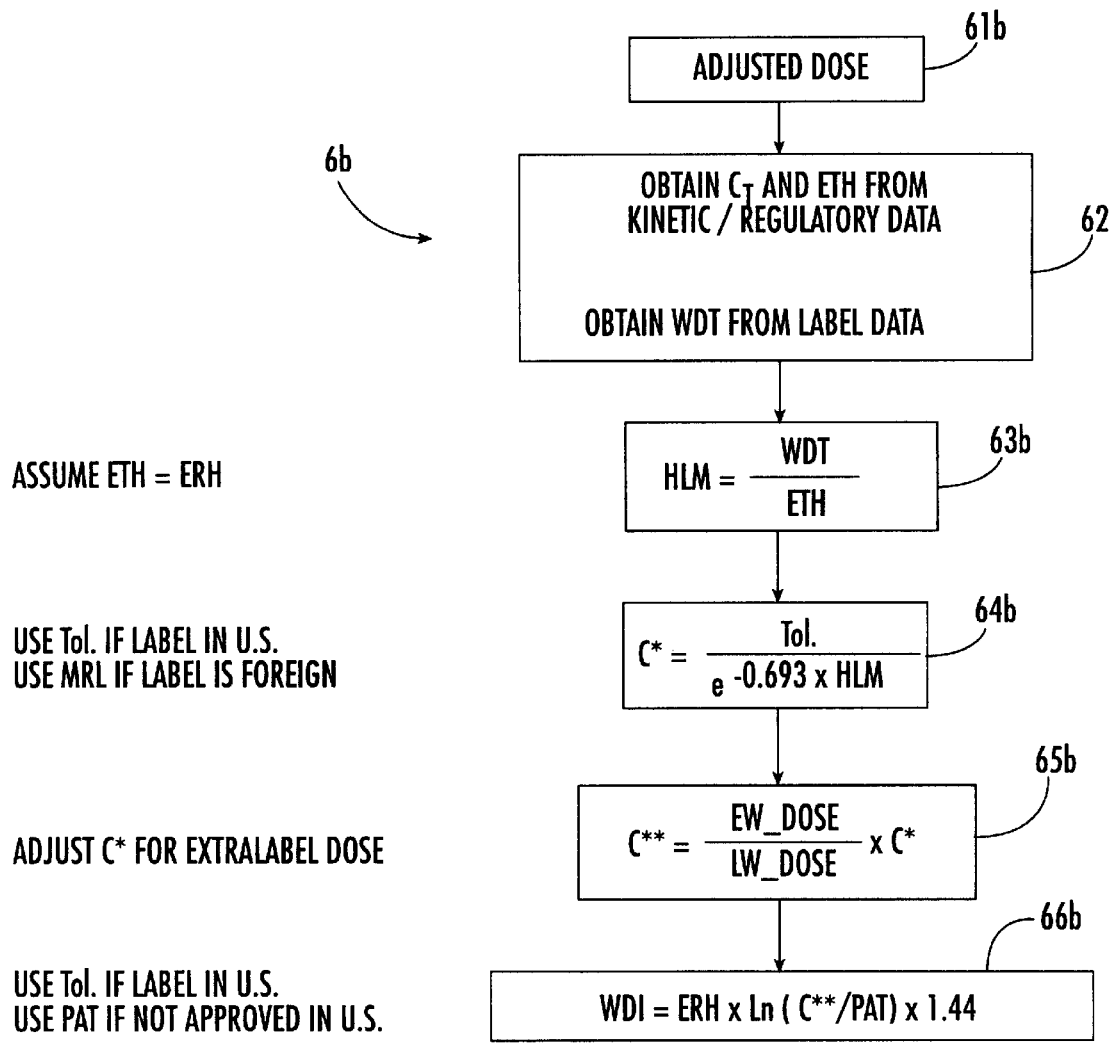
FIG. 6B illustrates operations performed by a second withdrawal interval estimator of an embodiment of the present invention, employed when kinetic/regulatory data are available.
Figure 6C:
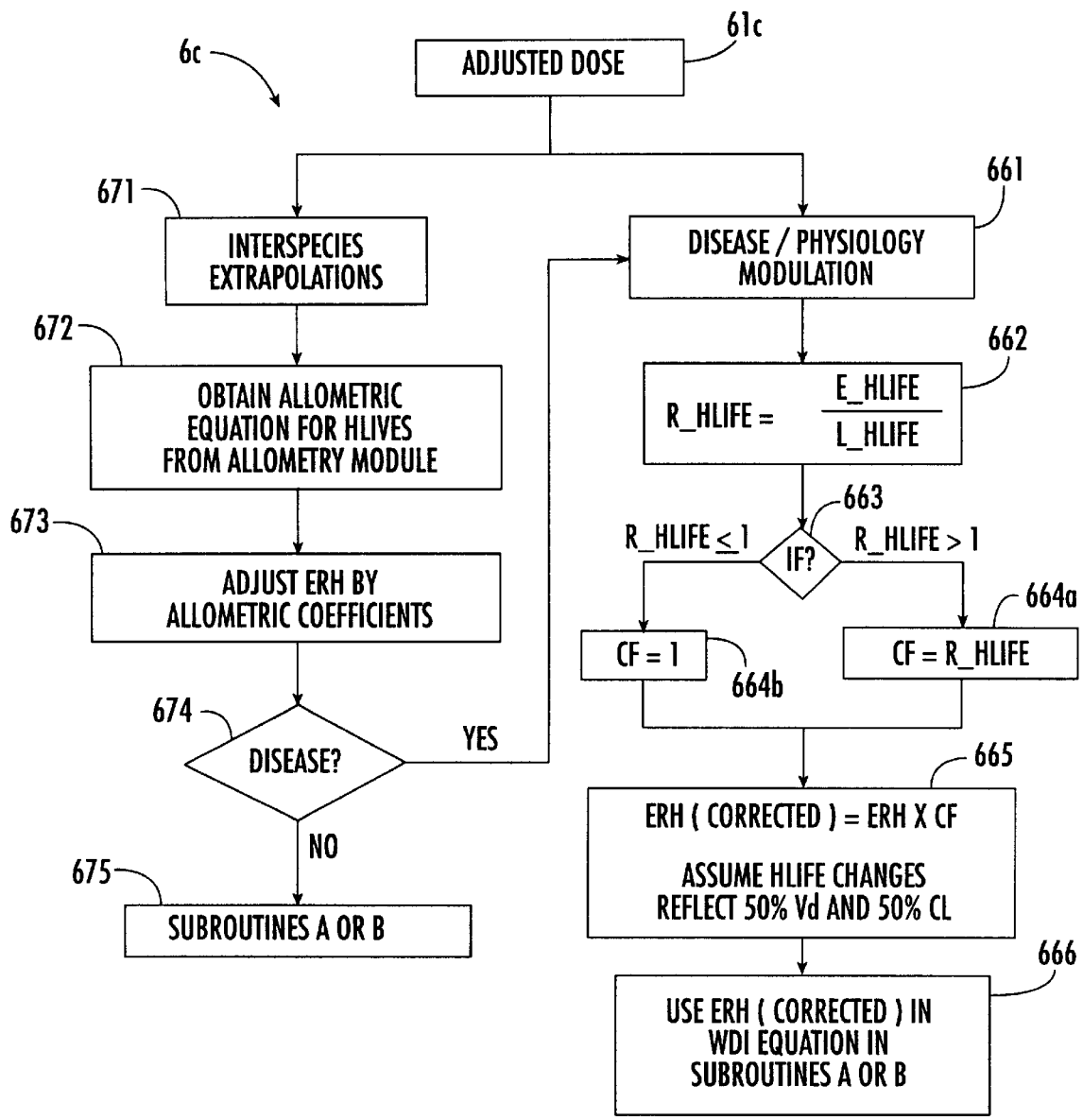
FIG. 6C illustrates operations performed by a withdrawal interval modifier of a preferred embodiment of the present invention.
Figure 6D:
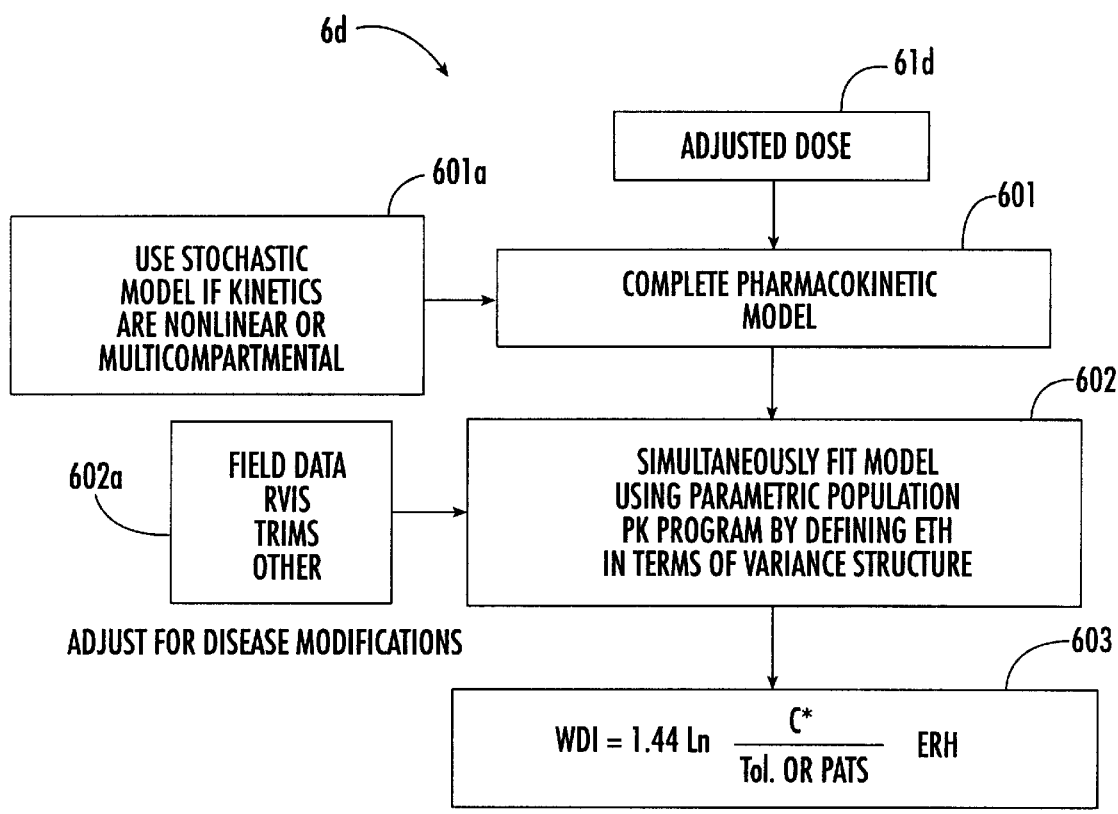
FIG. 6D illustrates operations performed by a withdrawal interval estimator of one embodiment of the present invention.
Figure 6E:
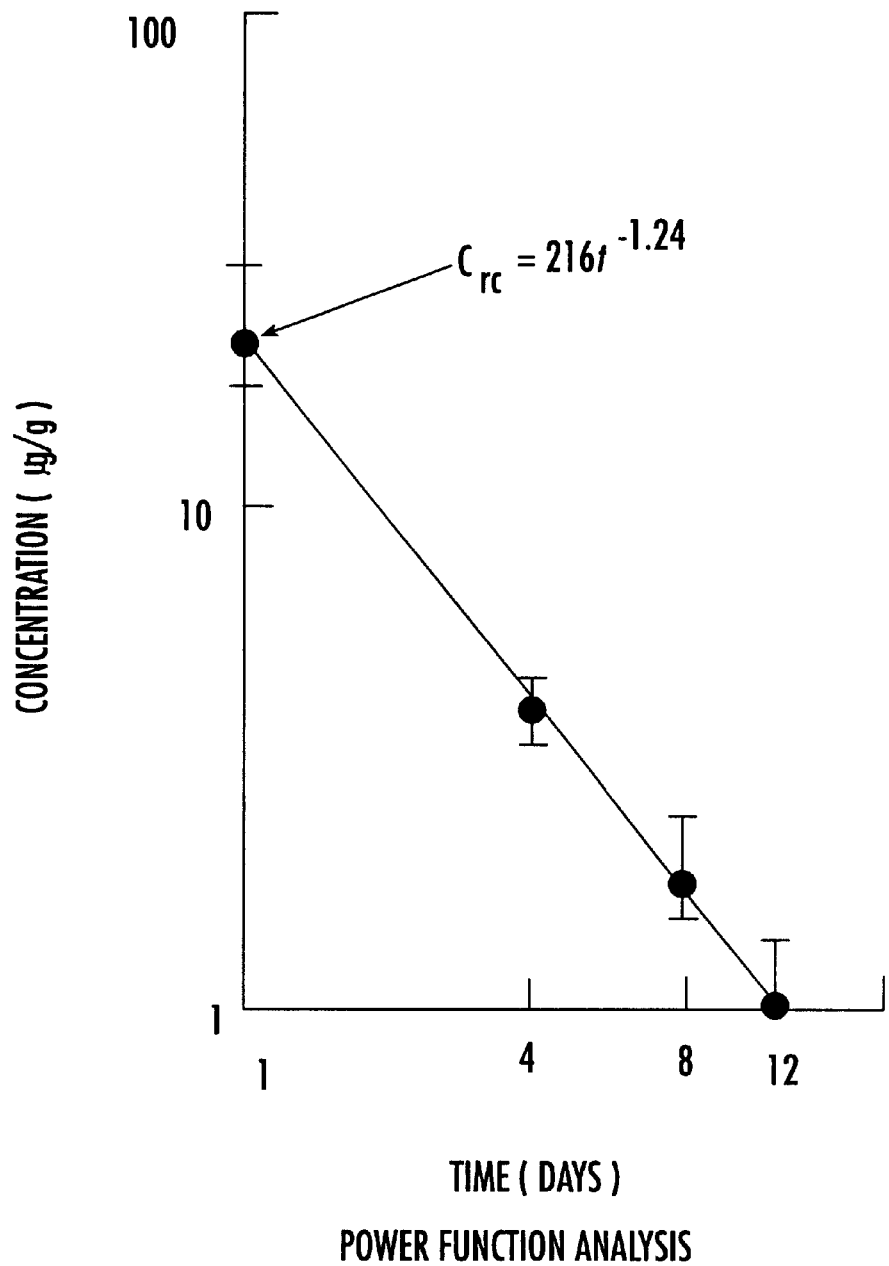
FIG. 6E illustrates an example of a stochastic power function analysis of tissue depletion which would describe a drug with polyexponential or nonlinear kinetics.

If data is available suggesting that tissue decay is non-linear (e.g. due to metabolism), then an analytical equation for decay is written or a stochastic power-function regression as outlined in the WDI modifier illustrated in 601a and FIGS. 6D–6E is used. If a specific pharmacokinetic model for the drug or chemical is known, then this model is directly used in estimator 601 (FIG. 6D block 601) and a WDI is calculated. This approach would describe the tissue depletion profile for a drug having any degree of complexity (e.g., nonlinear metabolism or tissue binding). However, for most drugs and dosages used in veterinary medicine, or contaminating compounds, first-order tissue depletion kinetics will be applicable.

In contrast, data extracted from label information reflects parameters estimated for the upper bound of a statistical confidence interval. In the US, this is the $99^{th}$ percentile estimated with an p<0.05. In data from other jurisdictions, such a regression approach is not used but the withdrawal time approved is assumed to reflect a similar degree of statistical confidence. The only assumption made is that the regulatory experimental design assures that the vast majority of animals slaughtered at the prescribed withdrawal time will be below the target tolerance or MRL 21. It is irrelevant whether this hypothesis is tested using parametric estimates of the tissue depletion regression function or non-parametric point estimates of a withdrawal time. The result is that the data obtained from a label package represents, for our purposes, the $99^{th}$ percentile of the $C_T$ and ETH, which we term C*, and is bounded by the line 22 defined by the virtual ERH (Effective Residue Half-life).

It will be appreciated that the extrapolating step can be carried out in any manner, and the corresponding extrapolating means implemented in any manner, such as by graphic computation, exponential computation, trigonometric computation, etc.

The EWE essentially takes a number of independent approaches to estimate these four parameters. Viewed in a different light, this approach is actually estimating the statistical properties (mean, variance) of $C_T$ and ETH. In the final implementation of this process (FIG. 6D; 602), this data is used in this manner and the output will simply be the $99^{th}$ percentile of the disposition function to calculate a $WDI_{99}$ (603). Population pharmacokinetics and Bayesian estimation algorithms allow this process to be implemented in a manner that may be validated with field observations (e.g., feedback data in the form of tissue samples from animals after slaughter).

The problem is to determine how long it takes for drug to deplete from $C_T$ to tolerance. At this stage, the estimators employed in FIG. 6A and FIG. 6B are used to independently estimate these parameters and then calculate WDIs for each process. As will be seen, in FIG. 6a the half life multiplier is assumed, while in FIG. 6b a $C_T$ and ETH are obtained from kinetic or regulatory data 62. Otherwise, like components of FIGS. 6a and 6b are assigned like numbers. Both begin with input of an adjusted dose 61a, 61b. In block 64a, 64b, Tol. is used if the label data is US and MRL is used in its place if label data is foreign; in block 66a, 66b, Tol. is used if label data is US and PAT is used if the treatment is not approved in this country, or if the compound is an environmental contaminant (e.g., heptachlor, chlordane).

A critical factor calculated in this analysis is the half-life multiplier (HLM) which computes the number of ETHs or ERHs required to get from $C_T$ to tolerance. In FIG. 6a the initial estimate is the default kinetic assumption of 5 (97% eliminated). However, as more drug data is processed through EWE, this default parameter will be more accurately estimated and probably will become drug-class dependent at some point in the future. As shown in FIG. 6d, by decomposing the withdrawal time into its constitutive pharmacokinetic parameters, disease or physiological states (e.g. age) may be accounted for by using literature to determine their influence on ETH or CT (blocks 61d, 601, 601a, 602, 602a, 603).

Disease effects are partitioned across changes in volume of distribution and clearance to make our estimate more robust. (FIG. 6C, blocks 661, 662, 663, 664a, 664b, 665, 666) Similarly, when dose extrapolations are made across species, allometric exponents relating half-lives between species can be applied to ETH/ERH to adjust for the species being treated (FIG. 6C, blocks 671, 672, 673, 674, 675).

Returning to FIG. 2, the final step of the EWE process is to calculate the actual $99^{th}$ percentile starting tissue concentration (C**) which reflects the actual extralabel dosage used. This is obtained by adjusting the reference label C* by the working dosages calculated above (LW_Dose, EW_Dose). The problem now is merely to determining how long is required for drug to deplete from C** to target tolerance or PAT, that is the WDI, when depletion is governed by ERH. (see lines 23, 24 in FIG. 2). The above series of calculations are conducted on each tissue for both safety (PAR) and pharmacokinetic (ETH, $C_T$) endpoints. Multiple WDIs are determined and the longest one will be selected for recommendation. This process thus provides the regulatory statistical assurances and extrapolates the resulting $WDI_{99}$.

The final complication which could occur involves administering compound drugs or the same drug by multiple routes (e.g. intrammary and systemic). For different drugs, the longest WDI will be selected. For multiple routes, one approach is simply to use the principle of superposition and add the tissue depletion curves to obtain a combined WDI, implemented as a multiple drug/route adjuster module (FIG. 1; 5a).

Feedback and Validation: As can be appreciated from this process, there are a number of assumptions which may not hold for many drugs. The EWE process exemplified above is formulated as an iterative procedure which allows feedback from previous analyses or actual field observations to improve the estimate. For example, the more accurate the pharmacokinetic data, the better the WDI estimates in the processes of FIG. 6B and FIG. 6C. Similarly, the output from this process has regulatory and food safety impact. Thus, the EWE can be executed in a population pharmacokinetic environment where each parameter being estimated is linked to independent field or clinical data to improve the estimate. An additional strength of this approach is that as such data is modeled, the nature of the statistical distribution around the WDI will be obtained.

An optimal source of such data is available in the USDA-RVIS and FDA-TRIMS surveillance and monitoring databases. By inputting this data into EWE, the statistical confidence around EWE's WDI estimates will be achieved. This can be analyzed using both parametric and nonparametric statistical techniques. Use of this data also suggests that a primary use of the EWE process would be to design the monitoring and validation sampling strategies using estimated WDIs to determine under what circumstances and field use conditions residues would be most likely to occur. The primary difference between the parametric approach and the nonparametric approach is that the parametric model actually estimates ETH and CT directly and determines the nature of the statistical distribution operative. In contrast, the nonparametric model only allows as input concentrations that are above tolerance/PAT (+) or below (−). What is being tested is simply whether $WDI_{99}$ can differentiate the breakpoint between + and −. This is equivalent to conducting a slaughter test (as has been done in some countries) and taking the withdrawal time as that which occurs when all animals are below MRL. (Note that a recent series of papers by Concordet and Toutain {$J$ $Vet.$ $Pharmacol.$ $Therap.$ 20: 374–379; 380–386, 1997} derive nonparametric statistical tests to accomplish this). It is not suggested herein whether a parametric regression or nonparametric approach is superior to simply validate a WDI. In contrast, the implementation of these tests would ultimately improve the underlying model used to calculate the WDI. Other sources of data could include the individual animal results from a screening assay; producer group's quality assurances programs where recommended WDIs could be validated under various dose conditions. Similarly, data submitted from industry research could improve these models. A final scenario is that a small sample of veterinarians requesting WDIs from FARAD would be requested to send back samples for validation.

Implementation: The invention is executed in a Visual-Basic database program that has regulatory and pharmacokinetic data modules. Specific files for input of data can include the following:

1. A file of approved label drugs with dosages, indications and withdrawal times for US and Foreign countries.
2. A file tabulating pharmacokinetic data based on "experiments" resulting from analysis of data for a specific dose, route, matrix, and disease in a species.
3. A file of US approved tissue tolerances and safe concentrations; Foreign drug approvals; Validated EWE-calculated PATs.
4. A file of screening tests, official FSIS/FDA assays with LOQs and statistics which can be directly implemented in the population model.
5. A tabulation of US and Foreign ADIs.
6. A summary datafile storing interspecies allometric coefficients and mean pharmacokinetic data.
7. A bridging database which obtains EWE usable dose, concentration-time data extracted from databases such as RVIS/TRIMS.
8. A file containing the results of validated WDI estimates.

In conclusion, the present invention is useful for extending the estimation of validated WDIs for extralabel drug use to be used as approved WDTs under the new flexible labeling guidelines since a defensible statistical inference procedure is available. The same approach can be used to establish approved WDTs for minor species uses. EWE can also be used to extrapolate WDIs based on foreign MRLs or LOQs in those cases where "zero-residue" policies are operative, for use by US producers exporting to those countries. In the context of a global FARAD, this process can be used to cross-extrapolate between any two countries as long as PARs for the country of use could be adequately defined. The invention can also be used as a development tool to design experiments to support formal regulatory data packages or help establish WDTs for "flexible-label" products. Finally, the invention can be used for approval of any withdrawal time submission in lieu of repeated slaughter studies.

The present invention is explained in greater detail in the following non-limiting Examples.

EXAMPLE 1

Computation of a WDI from Regulatory Data

A simulation was conducted to demonstrate the similarity between the WDI predictions obtained by the EWE method (Procedure B). and the WDT determined by the FDA official method. The FDA method to establish withdrawal times is based on a statistical Tolerance Limit procedure, and has been published in the *Guideline for Establishing a Withdrawal Period* (Center for Veterinary Medicine). This guideline contains a real example on how the FDA establishes WDT. The instructions contained in this example were used to carry out the simulation described herein.

FDA Tolerance Limit Procedure. Drug tissue concentrations at slaughter time from twenty-five animals are obtained. target tissues from animals are sampled in groups of five at five different sampling times according to the depletion characteristics of the drug. A regression analysis is then conducted and a series of tests are performed to verify the validity of the assumptions implied by the statistical method. The first step is to assess whether any data point falls on the linear part of the depletion curve for the phase of the curve closest to the MRL or Tolerance. All data points are supposed to be above the validated LOQ of the analytical method for any statistical inference to be acceptable. The next step is to assure the constancy of variances for each datapoint (homoscedasticity). Bartlett's test is used to check on this point, although the guideline states that other methods can be used instead. Finally, an ANOVA test is conducted to verify the log-linearity of the regression line.

When the regression line is shown to conform to the statistical assumptions, a set of calculations is conducted to establish the tolerance limit for a "candidate" withdrawal time, according to the method of Owen. This initial WDT is established arbitrarily, and if for that candidate withdrawal time the tolerance limit exceeds the permitted Tolerance, then the calculation is repeated adding one day to the previous candidate WDT. This process is repeated until the tolerance limit falls under the official Tolerance for a particular WDT. This last candidate is established as the official WDT.

Simulations. The following pharmacokinetic and dosing conditions were established for the initial simulations: The label dose was 400 mg, administered as a single intravenous bolus dose. The elimination rate in the target tissue was 0.1155 day$^{-1}$, the volume of distribution of the central compartment was 11.67 liters. The tissue plasma ratio was 2.7. The label tolerance was 17 ppm. The variance of the concentration, expressed in logarithmic scale, was 0.071. With these conditions 1000 individusld (5 datapoints each) were simulated (5000 datapoints). Out of all these, 25 datapoints were selected randomly (5 datapoints per time). The WDT established by the FDA method for this group of animals using the Tolerance Limit method above was 23 days. By using the elimination constant (Kel, or slope of the regression line) as the only input into the EWE process a WDI of 22.95 was predicted for the same group of animals, dosing, and tolerance conditions (see Table 1).

This example demonstrates that the EWE process sets a WDI similar to the official WDT under the same dosing conditions, when the slope of the regression curve is known (from literature or regulatory data).

EXAMPLE 2

Computation of an Extra-Label WDI from Regulatory Data

This example was conducted to assess how well the EWE process would predict a WDI for an extralabel use. This simulation, called EWESIN_2, was set with the following conditions: dose was increased to 1000 mg and the extra-label Tolerance (different of the label MRL, if foreign) was 12 ppm. The same slope was used as in Example 1, since that would be the procedure followed in practice: obtain that information from label, regulatory or literature data and apply to all calculations. The WDI was set to 34.41. In order to validate this result we simulated again 1000 animals and 5,000 datapoints using the same level of variance, the same Pk parameters and the new dose of 1000 mg. We selected randomly 25 datapoints from 25 animals and applied the Tolerance Limit procedure aiming at a new Tolerance: 12 ppm. Again, the result was 34 days. See Table 2. The biologically insignificant differences between EWE-predicted WDIs and the Tolerance Limit Procedure WDT is based on random errors inherent to sampling 25 data points from a population of 5,000 simulated data points.

EXAMPLE 3

Computation of an Extra-Label WDI from Regulatory Data with Disease Affecting Clearance Another simulation was conducted with the same 1000 mg and 12 ppm of tolerance as before, with the half-life arbitrarily increased 1.73-fold. Assuming the increase in half-life was due entirely to a decrease in clearance, the estimate of WDI obtained by the EWE process was 58.5 days (see Table 3). Assuming monoexponential decay of drug in the target tissue, an increase of half-life that is totally due to clearance can be formulated as:

$$Kel^{**} = Kel_{label}/CF$$

$$Vd^{**} = Dose_{label}/C^*$$

where $Kel^{}$ is the elimination rate constant in disease conditions, $Kel_{label}$ is the elimination rate constant in normal conditions, CF is the ratio of half-lives, or correction factor, $Vd^{}$ is the virtual volume of distribution in tissue (including the statistical confidence limit) under disease conditions, and $C^*$ has been defined previously. We again simulated 1000 tissue depletion curves with 5000 datapoints and selected 25 randomly. This simulation was called EWESIM_3. The FDA's Tolerance Limit procedure was applied to these data and the result was a WDT of 61 days (Table 3).

EXAMPLE 4

Computation of an Extra-Label WDI from Regulatory Data with Disease Affecting Volume of Distribution This example, called EWESIN_4, is essentially the same as Example 3, except that it was assumed that the increase in half-life was due entirely to an increase in volume. The WDI obtained by EWE was 50.32 days (see Table 4). The Tolerance Limit procedure established 49 days as the WDT based on 25 randomly selected datapoints from a simulated dataset consisting of 5,000 samples (Table 4).

The effect of volume change on half-life for this example can be formulated as:

$$Kel^{**} = Kel_{label}/CF$$

$$Vd^{**} = (Dose_{label}/C^*) \times CF$$

where $Kel^{}$ is the elimination rate constant in disease conditions, Kellabel is the elimination rate constant in normal conditions, CF is the ratio of half-lives, or correction factor, $Vd^{}$ is the virtual volume of distribution in tissue (including the statistical confidence limit) under disease conditions, and $C^*$ has been defined previously.

EXAMPLE 4

Computation of an Extra-Label WDI from Regulatory Data with Disease Affecting Both Clearance and Volume of Distribution Finally the same type of simulation as in Examples 3 and 4 was accomplished but this time, the increase in half life by a factor of 1.7 was partially due to an increase in Vd and partially due to a decrease in clearance (fifth-fifty). This example, called EWESIN_5, estimated a WDI of 53.87 days while the Tolerance Limit Procedure established the WDT at 54 days. Results are given in Table 5. This simulation was formulated as:

$$Kel^{**} = Kel_{label}/CF$$

$$Vd^{**} = Dose_{label}/C^* (1 + ((CF-1)/2))$$

where $Kel^{}$ is the elimination rate constant in disease conditions, $Kel_{label}$ is the elimination rate constant in normal conditions, CF is the ratio of half-lives, or correction factor, $Vd^{}$ is the virtual volume of distribution in tissue (including the statistical confidence limit) under disease conditions, and $C^*$ has been defined previously.

Note that concomitant changes in volume of distribution and clearance by factors different from 50% of the initial value can also be allowed by simply partitioning the total 100% of change in the value of half-life differentially between clearance and volume of distribution The foregoing is illustrative of the present invention, and is not to be construed as limiting thereof. The invention has been explained above primarily with respect to drugs, but it may also be used for other compounds administered to animals deliberately or inadvertently, such as pesticides and environmental contaminants. In addition, the invention has largely been explained for practice within the United States using the regulatory nomenclature of the United States, but the invention is not limited to any particular regulatory nomenclature and can be practiced in other jurisdictions in accordance with the regulatory nomenclature of those jurisdictions.

TABLE 1

Dose Equals 400 mg
EWESIN_1. Computation of WDT and WDI from regulatory (FDA) data.

1. Computation of WDT and WDI from regulatory (label) data.

| WDT | CONC (ppm) | Ln Conc | | WDT | Avg Conc | Avg Ln C | Variance | Ln Var |
|---|---|---|---|---|---|---|---|---|
| 3 | 62.3451 | 4.133 | | 3 | 62.631 | 4.129 | 0.021 | −3.861 |
| 3 | 49.2054 | 3.896 | | 7 | 40.791 | 3.695 | 0.034 | −3.377 |
| 3 | 67.3542 | 4.210 | | 12 | 22.924 | 3.097 | 0.088 | −2.434 |
| 3 | 72.3654 | 4.282 | | 20 | 9.235 | 2.192 | 0.077 | −2.567 |
| 3 | 61.875 | 4.125 | | 30 | 3.409 | 1.176 | 0.133 | −2.017 |
| 7 | 31.462 | 3.449 | | 14.4 | 27.797788 | 2.858 | 0.071 | −2.851 |
| 7 | 40.432 | 3.700 | | | | | | |
| 7 | 47.1254 | 3.853 | | FDA Tolerance Limit Method calculations: | | | | |
| 7 | 35.9694 | 3.583 | $a =$ | 4.444 | $BDSS =$ 1502 | | $u =$ | 1.656 |
| 7 | 48.9658 | 3.891 | $b =$ | −0.110 | $d =$ | 7.788 | $k =$ | 10.927 |
| 12 | 16.204 | 2.785 | $s^2 =$ | 0.062 | $z =$ | 2.326 | $Tol_{lim} =$ | 2.726 |
| 12 | 24.2671 | 3.189 | $s =$ | 0.250 | $t_{ave} =$ | 14.400 | $\exp(t_{lim}) =$ | 15.279 |
| 12 | 16.8401 | 2.824 | $df =$ | 23.000 | $[\ldots]^{1/2} =$ | 0.299 | $Tol =$ | 17.000 |
| 12 | 24.1904 | 3.186 | $n =$ | 25.000 | $[\ldots] =$ | 0.089 | | |
| 12 | 33.1178 | 3.500 | $MDW =$ | 14.400 | $n =$ | 0.043 | $WDT =$ | 23.00 |
| 20 | 7.1254 | 1.964 | | | | | | |
| 20 | 8.6325 | 2.156 | | EWE Process calculations: | | | | |
| 20 | 6.69325 | 1.901 | $LW\_dose =$ | 400.00 | $Co =$ | 31.51 | $ERH =$ | 6.29 |
| 20 | 10.8457 | 2.384 | $EW\_dose =$ | 400.00 | $TPR =$ | 2.70 | $WDT_{50} =$ | 14.60 |
| 20 | 12.877 | 2.555 | $MRL =$ | 17 | $CT_{label} =$ | 85.07 | $HLM_{50} =$ | 2.32 |
| 30 | 4.6457 | 1.536 | $Tol =$ | 17 | $V_c =$ | 12.69 | $HLM_{99} =$ | 3.65 |
| 30 | 3.50124 | 1.253 | $L\_Hlife =$ | 6.29 | $Kel =$ | 0.11 | $C^* =$ | 213.90 |
| 30 | 2.57400 | 0.945 | $R\_Hlife =$ | 1.00 | $ETH =$ | 6.29 | $C^{**} =$ | 213.90 |
| 30 | 4.3658 | 1.474 | $E\_Hlife =$ | 6.29 | $CF =$ | 1.00 | $WDI =$ | 22.95 |
| 30 | 1.956 | 0.671 | | | | | | |

2. Bartlett's Test for Homogeneity of the Variances $(s_i)^2$ = Variance of Ln concentration in $i^{th}$ group
$g$ = Number of Withdrawal groups = 5
$f$ = Common # of df for variance estimate = 4

| Time | $(s_i)$ | $Ln(s_i)^2$ | $f_i$ | $f_i s_i^2$ | $f_i Lns_i^2$ | $1/f_i - 1$ |
|---|---|---|---|---|---|---|
| 3 | 0.o21 | −3.861 | 4 | 0.0841984 | −15.443495 | 0.333333 |
| 7 | 0.034 | −3.377 | 4 | 0.1366323 | −13.507025 | 0.333333 |
| 12 | 0.088 | −2.434 | 4 | 0.350707 | −9.7363939 | 0.333333 |
| 20 | 0.077 | −2.567 | 4 | 0.3069551 | −10.269392 | 0.333333 |
| 30 | 0.133 | −2.017 | 4 | 0.5324635 | −8.0661409 | 0.333333 |
| SUMS = | 0.353 | −14.256 | 20 | 1.4109564 | −57.022447 | 1.666667 |
| M = | 3.99315665 | | | | | |
| C = | 1.00694444 | | | | | |
| $X^2_{g-1} =$ | 3.96561764 | | | | | |
| M/C = | 3.96561764 | | | | | |
| P = | >0.25 | | | | | |

TABLE 2

Dose equals 1000 mg.
EWESIN_2: Simulation for WDI determination for WDT data.

1. Tolerance limit and EWE procedures. No disease effect. Extralabel dose 3 times label dose.

| WDT | CONC (ppm) | Ln Conc | | WDT | Avg Conc | Avg Ln C | Variance | Ln Var |
|---|---|---|---|---|---|---|---|---|
| 3 | 169.37 | 5.132 | | 3 | 161.368 | 5.076 | 0.021 | −3.879 |
| 3 | 171.37 | 5.144 | | 7 | 101.281 | 4.605 | 0.032 | −3.429 |
| 3 | 187.33 | 5.233 | | 12 | 57.831 | 4.038 | 0.049 | −3.011 |
| 3 | 149.42 | 5.007 | | 20 | 23.127 | 3.089 | 0.129 | −2.051 |
| 3 | 129.37 | 4.863 | | 30 | 7.737 | 2.000 | 0.133 | −2.178 |
| 7 | 114.52 | 4.741 | | 14.4 | 70.26864 | 3.761 | 0.069 | −2.910 |
| 7 | 91.29 | 4.514 | | | | | | |

TABLE 2-continued

Dose equals 1000 mg.
EWESIN_2: Simulation for WDI determination for WDT data.

| | | | | | | | | |
|---|---|---|---|---|---|---|---|---|
| 7 | 76.97 | 4.343 | | | FDA Tolerance Limit Method calculations: | | | |
| 7 | 103.66 | 4.641 | a = | 5.406 | BDSS = | 1502 | u = | 1.656 |
| 7 | 119.97 | 4.787 | b = | −0.114 | d = | 4.278 | k = | 6.586 |
| 12 | 77.07 | 4.345 | $s^2$ = | 0.060 | z = | 2.326 | $Tol_{lim}$ = | 2.401 |
| 12 | 43.22 | 3.766 | s = | 0.245 | $t_{ave}$ = | 14.400 | $exp(t_{lim})$ = | 11.037 |
| 12 | 50.27 | 3.917 | df = | 23.000 | $[\ldots]^{1/2}$ = | 0.544 | Tol = | 12.000 |
| 12 | 63.69 | 4.154 | n = | 25.000 | $[\ldots]$ = | 0.296 | | 23.000 |
| 12 | 54.91 | 4.006 | MDW = | 14.000 | n = | 0.043 | WDT = | 34.00 |
| 20 | 21.12 | 3.050 | | | | | | |
| 20 | 19.87 | 2.989 | | | EWE Process calculations: | | $V_d$** = | 1.87 |
| 20 | 23.93 | 3.175 | LW_dose = | | Co = | | ERH = | 6.29 |
| 20 | 37.02 | 3.612 | EW_dose = | | TPR = | | $WDT_{50}$ = | 14.59 |
| 20 | 13.70 | 2.617 | MRL = | | $CT_{label}$ = | | $HLM_{50}$ = | 2.32 |
| 30 | 6.06 | 1.801 | Tol = | | $V_c$ = | | $HLM_{99}$ = | 3.65 |
| 30 | 5.32 | 1.672 | L_Hlife = | | Kel = | | C* = | 213.90 |
| 30 | 9.94 | 2.297 | R_Hlife = | | ETH = | | C** = | 534.76 |
| 30 | 11.29 | 2.424 | E_Hlife = | | CF = | | WDI = | 34.41 |
| 30 | 6.08 | 1.804 | | | | | | |

2. Bartlett's Test for Homogeneity of the Variances $(s_i)^2$ = Variance of Ln concentration in $i^{th}$ group
g = Number of Withdrawal groups = 5
f = Common # of df for variance estimate = 4

| Time | $(s_i)$ | $Ln(s_i)^2$ | $f_i$ | $f_i s_i^2$ | $f_i Lns_i^2$ | $1/f_i - 1$ |
|---|---|---|---|---|---|---|
| 3 | 0.021 | −3.879 | 4 | 0.082655 | −15.51747 | 0.333333 |
| 7 | 0.032 | −3.429 | 4 | 0.129618 | −13.71784 | 0.333333 |
| 12 | 0.049 | −3.011 | 4 | 0.196914 | −12.04514 | 0.333333 |
| 20 | 0.129 | −2.051 | 4 | 0.51454 | −8.203107 | 0.333333 |
| 30 | 0.113 | −2.178 | 4 | 0.453215 | −8.710733 | 0.333333 |
| SUMS = | 0.344 | −14.549 | 20 | 1.376942 | −58.19428 | 1.666667 |
| M = | 4.67693786 | | | | | |
| C = | 1.00694444 | | | | | |
| $X^2_{g-1}$ = | 4.64468312 | | | | | |
| M/C = | 4.64468312 | | | | | |
| P = | >0.25 | | | | | |

TABLE 3

Altered Clearance
EWESIN_3: simulation for WDI determination from WDT data. Impaired clearance.

1. Tolerance limit and EWE procedures. Disease affects clearance.

| WDT | CONC (ppm) | Ln Conc | | WDT | Avg Conc | Avg Ln C | Variance | Ln Var |
|---|---|---|---|---|---|---|---|---|
| 3 | 230.15 | 5.439 | | 3 | 189.528 | 5.232 | 0.031 | −3.479 |
| 3 | 171.41 | 5.144 | | 7 | 138.461 | 4.916 | 0.035 | −3.340 |
| 3 | 176.37 | 5.173 | | 12 | 106.177 | 4.647 | 0.047 | −3.049 |
| 3 | 151.25 | 5.019 | | 20 | 62.713 | 4.103 | 0.095 | −2.355 |
| 3 | 218.46 | 5.387 | | 30 | 30.804 | 3.378 | 0.133 | −2.015 |
| 7 | 167.35 | 5.120 | | 14.4 | 105.53668 | 4.455 | 0.068 | −2.848 |
| 7 | 131.66 | 4.880 | | | | | | |
| 7 | 122.89 | 4.811 | | | FDA Tolerance Limit Method calculations: | | | |
| 7 | 107.57 | 4.678 | a = | 5.430 | BDSS = | 1502 | u = | 1.656 |
| 7 | 162.85 | 5.093 | b = | −0.068 | d = | 1.909 | k = | 3.807 |
| 12 | 112.55 | 4.723 | $s^2$ = | 0.060 | z = | 2.326 | $Tol_{lim}$ = | 2.439 |
| 12 | 129.35 | 4.863 | s = | 0.245 | $t_{ave}$ = | 14.400 | $exp(t_{lim})$ = | 11.460 |
| 12 | 74.96 | 4.317 | df = | 23.000 | $[\ldots]^{1/2}$ = | 1.219 | Tol = | 12 |
| 12 | 119.55 | 4.784 | n = | 25.000 | $[\ldots]$ = | 1.486 | L_WDT = | 23.00 |
| 12 | 94.48 | 4.548 | MDW = | 14.400 | n = | 0.043 | WDT = | 61.00 |
| 20 | 83.24 | 4.422 | | | | | | |
| 20 | 38.54 | 3.652 | | | Kel** = | | | 0.06 |
| 20 | 51.10 | 3.934 | | | EWE Process calculations: | | $V_d$** = | 18.7 |

TABLE 3-continued

Altered Clearance
EWESIN_3: simulation for WDI determination from WDT data. Impaired clearance.

| | | | | | | | | |
|---|---|---|---|---|---|---|---|---|
| 20 | 69.46 | 4.241 | LW_dose = | 400.00 | Co = | 31.51 | ERH = | 10.70 |
| 20 | 71.23 | 4.266 | EW_dose = | 1000.00 | TPR = | 2.70 | $WDT_{50}$ = | 14.59 |
| 20 | 29.68 | 3.390 | MRL = | 17 | $CT_{label}$ = | 85.07 | $HLM_{50}$ = | 2.32 |
| 30 | 37.25 | 3.618 | Tol = | 12 | $V_c$ = | 12.70 | $HLM_{99}$ = | 3.65 |
| 30 | 42.90 | 3.759 | L_Hlife = | 6.29 | Kel = | 0.11 | C* = | 213.90 |
| 30 | 16.54 | 2.806 | R_Hlife = | 1.70 | ETH = | 6.29 | C** = | 534.76 |
| 30 | 27.66 | 3.320 | E_Hlife = | 10.70 | CF = | 1.70 | WDI = | 58.49 |

2. Bartlett's Test for Homogeneity of the Variances $(s_i)^2$ = Variance of Ln concentration in $i^{th}$ group
g = Number of Withdrawal groups = 5
f = Common # of df for variance estimate = 4

| Time | $(s_i)$ | $Ln(s_i)^2$ | $f_i$ | $f_i s_i^2$ | $f_i Lns_i^2$ | $1/f_i - 1$ |
|---|---|---|---|---|---|---|
| 3 | 0.031 | −3.479 | 4 | 0.123308 | −13.91745 | 0.333333 |
| 7 | 0.035 | −3.340 | 4 | 0.141763 | −13.35956 | 0.333333 |
| 12 | 0.047 | −3.049 | 4 | 0.189656 | −12.19535 | 0.333333 |
| 20 | 0.095 | −2.355 | 4 | 0.37944 | −9.421417 | 0.333333 |
| 30 | 0.133 | −2.015 | 4 | 0.5333359 | −8.059422 | 0.333333 |
| SUMS = | 0.342 | −14.238 | 20 | 1.367526 | −56.9632 | 1.666667 |
| M = | 3.2986171 | | | | | |
| C = | 1.0069444 | | | | | |
| $X^2_{g-1}$ = | 3.275868 | | | | | |
| M/C = | 3.275868 | | | | | |
| P = | >0.25 | | | | | |

TABLE 4

Altered Volume
EWESIN_4: simulation for WDI determinations from WDT data. Increased volume.

1. Tolerance limit and EWE procedures. Disease affects volume of distribution.

| WDT | CONC (ppm) | Ln Conc | | WDT | Avg Conc | Avg Ln C | Variance | Ln Var |
|---|---|---|---|---|---|---|---|---|
| 3 | 122.531 | 4.808 | | 3 | 105.761 | 4.654 | 0.018 | −4.032 |
| 3 | 95.2303 | 4.556 | | 7 | 90.159 | 4.486 | 0.041 | −3.190 |
| 3 | 104.649 | 4.651 | | 12 | 58.204 | 4.019 | 0.112 | −2.188 |
| 3 | 116.997 | 4.762 | | 20 | 34.026 | 3.493 | 0.097 | −2.334 |
| 3 | 89.3995 | 4.493 | | 30 | 15.987 | 2.739 | 0.089 | −2.423 |
| 7 | 64.36 | 4.164 | | 14.4 | 60.82741 | 3.878 | 0.071 | −2.833 |
| 7 | 86.5168 | 4.460 | | | | | | |
| 7 | 102.709 | 4.632 | | FDA Tolerance Limit Method calculations: | | | | |
| 7 | 108.254 | 4.684 | a = | 4.919 | BDSS = | 1502 | u = | 1.656 |
| 7 | 88.9545 | 4.488 | b = | −0.072 | d = | 2.543 | k = | 4.535 |
| 12 | 69.257 | 4.238 | $s^2$ = | 0.064 | z = | 2.326 | $Tol_{lim}$ = | 2.428 |
| 12 | 84.58 | 4.438 | s = | 0.253 | $t_{ave}$ = | 14.400 | $exp(t_{lim})$ = | 11.338 |
| 12 | 42.865 | 3.758 | df = | 23.000 | [...]$^{1/2}$ = | 0.915 | Tol = | 12 |
| 12 | 37.445 | 3.623 | n = | 25.000 | [...] = | 0.837 | L_WDT = | 23.00 |
| 12 | 56.8724 | 4.041 | MDW = | 14.400 | n = | 0.043 | WDT = | 49.00 |
| 20 | 32.956 | 3.495 | | | | | | |
| 20 | 19.245 | 2.957 | | | | | Kel** = | 0.06 |
| 20 | 41.254 | 3.720 | | EWE Process calculations: | | | Vd** = | 3.18 |
| 20 | 36.932 | 3.609 | LW_dose = | 400.00 | Co = | 31.51 | ERH = | 10.70 |
| 20 | 39.7448 | 3.682 | EW_dose = | 1000.00 | TPR = | 2.70 | $WDT_{50}$ = | 14.59 |
| 30 | 18.054 | 2.893 | MRL = | 17 | $CT_{label}$ = | 85.07 | $HLM_{50}$ = | 2.32 |
| 30 | 20.118 | 3.002 | Tol = | 12 | $V_c$ = | 12.70 | $HLM_{99}$ = | 3.65 |
| 30 | 13.845 | 2.628 | L_Hlife = | 6.29 | Kel = | 0.11 | C* = | 213.90 |
| 30 | 9.658 | 2.268 | R_Hlife = | 1.70 | ETH = | 6.29 | C** = | 314.56 |
| 30 | 18.258 | 2.905 | E_Hlife = | 10.70 | CF = | 1.70 | WDI = | 50.32 |

2. Bartlett's Test for Homogeneity of the Variances $(s_i)^2$ = Variance of Ln concentration in $i^{th}$ group

TABLE 4-continued

Altered Volume
EWESIN_4: simulation for WDI determinations from WDT data. Increased volume.

g = Number of Withdrawal groups = 5
f = Common # of df for variance estimate = 4

| Time | $(s_i)$ | $Ln(s_i)^2$ | $f_i$ | $f_i s_i^2$ | $f_i Lns_i^2$ | $1/f_i - 1$ |
|---|---|---|---|---|---|---|
| 3 | 0.018 | −4.032 | 4 | 0.070965 | −16.1274 | 0.333333 |
| 7 | 0.041 | −3.190 | 4 | 0.164711 | −12.7594 | 0.333333 |
| 12 | 0.112 | −2.188 | 4 | 0.448675 | −8.751 | 0.333333 |
| 20 | 0.097 | −2.334 | 4 | 0.387822 | −9.33401 | 0.333333 |
| 30 | 0.089 | −2.432 | 4 | 0.3546 | −9.69223 | 0.333333 |
| SUMS = | 0.357 | −14.166 | 20 | 1.426774 | −56.6641 | 1.666667 |
| M = | 3.8577769 | | | | | |
| C = | 1.0069444 | | | | | |
| $X^2_{g-1}$ = | 3.8311716 | | | | | |
| M/C = | 3.8311716 | | | | | |
| P = | >0.25 | | | | | |

TABLE 5

Altered Clearance and Altered Volume
EWESIN_5: simulation for WDI determination from label data. 50% increased Vd, 50% decreased clearance.

1. Tolerance limit and EWE procedures. Disease affects equally clearance and volume of distribution.

| WDT | CONC (ppm) | Ln Conc | | WDT | Avg Conc | Avg Ln C | Variance | Ln Var |
|---|---|---|---|---|---|---|---|---|
| 3 | 135.213 | 4.907 | | 3 | 136.896 | 4.912 | 0.018 | −4.007 |
| 3 | 119.54 | 4.784 | | 7 | 109.783 | 4.686 | 0.033 | −3.425 |
| 3 | 121.568 | 4.800 | | 12 | 76.948 | 4.341 | 0.070 | −2.664 |
| 3 | 166.955 | 5.118 | | 20 | 44.546 | 3.757 | 0.102 | −2.285 |
| 3 | 141.203 | 4.950 | | 30 | 21.876 | 3.033 | 0.132 | −2.028 |
| 7 | 132.25 | 4.885 | | 14.4 | 78.40978 | 4.146 | 0.071 | −2.882 |
| 7 | 106,528 | 4.668 | | | | | | |
| 7 | 86.525 | 4.460 | | FDA Tolerance Limit Method calculations: | | | | |
| 7 | 127.258 | 4.846 | a = | 5.159 | BDSS = | 1502 | u = | 1.656 |
| 7 | 96.354 | 4.568 | b = | −0.070 | d = | 2.234 | k = | 4.179 |
| 12 | 107.25 | 4.675 | $s^2$ = | 0.062 | z = | 2.326 | $Tol_{lim}$ = | 2.444 |
| 12 | 93.67 | 4.540 | s = | 0.249 | $t_{ave}$ = | 14.400 | $exp(t_{lim})$ = | 11.517 |
| 12 | 61.25 | 4.115 | df = | 23.000 | $[\ldots]^{1/2}$ = | 1.041 | Tol = | 12 |
| 12 | 74.205 | 4.307 | n = | 25.000 | $[\ldots]$ = | 1.084 | L_WDT = | 23.00 |
| 12 | 58.365 | 4.067 | MDW = | 14.400 | n = | 0.043 | WDT = | 54.00 |
| 20 | 51.895 | 3.949 | | | | | | |
| 20 | 29.657 | 3.390 | | | | | $Kel^{**}$ = | 0.06 |
| 20 | 48.58 | 3.883 | | EWE Process calculations: | | | $Vd^{**}$ = | 2.52 |
| 20 | 61.05 | 4.112 | LW_dose = | 400.00 | Co = | 31.51 | ERH = | 10.70 |
| 20 | 31.547 | 3.451 | EW_dose = | 1000.00 | TPR = | 2.70 | $WDT_{50}$ = | 14.59 |
| 30 | 16.3521 | 2.794 | MRL = | 17 | $CT_{label}$ = | 85.07 | $HLM_{50}$ = | 2.32 |
| 30 | 20.9217 | 3.041 | Tol = | 12 | $V_c$ = | 12.70 | $HLM_{99}$ = | 3.65 |
| 30 | 33.17 | 3.502 | L_Hlife = | 6.29 | Kel = | 0.11 | $C^*$ = | 213.90 |
| 30 | 25.7208 | 3.237 | R_Hlife = | 1.70 | ETH = | 6.29 | $C^{**}$ = | 396.12 |
| 30 | 12.2169 | 2.581 | E_Hlife = | 10.70 | CF = | 1.70 | WDI = | 53.87 |

2. Bartlett's Test for Homogeneity of the Variances $(s_i)^2$ = Variance of Ln concentration in $i^{th}$ group
g = Number of Withdrawal groups = 5
f = Common # of df for variance estimate = 4

| Time | $(s_i)$ | $Ln(s_i)^2$ | $f_i$ | $f_i s_i^2$ | $f_i Lns_i^2$ | $1/f_i - 1$ |
|---|---|---|---|---|---|---|
| 3 | 0.018 | −4.007 | 4 | 0.072719 | −16.02976 | 0.333333 |
| 7 | 0.033 | −3.425 | 4 | 0.130255 | −13.698232 | 0.333333 |
| 12 | 0.070 | −2.664 | 4 | 0.278668 | −10.65611 | 0.333333 |
| 20 | 0.102 | −2.285 | 4 | 0.40694 | −9.141534 | 0.333333 |
| 30 | 0.132 | −2.028 | 4 | 0.52642 | −8.111798 | 0.333333 |
| SUMS = | 0.354 | −14.409 | 20 | 1.415003 | −57.63744 | 1.666667 |

TABLE 5-continued

Altered Clearance and Altered Volume
EWESIN_5: simulation for WDI determination from label data. 50% increased Vd, 50% decreased clearance.

| | |
|---|---|
| M = | 4.6654252 |
| C = | 1.0069444 |
| $X^2_{g-1}$ = | 4.6332499 |
| M/C = | 4.6332499 |
| P = | >0.25 |

We claim:

1. A method of estimating a withdrawal interval for an adjusted dose of a compound from a prior withdrawal time for a corresponding prior dose of said compound, corresponding prior half-life data and a tolerance concentration, for a tissue of interest, said method comprising the following steps that are performed in a data processing system:

accepting selection of an adjusted dose for said compound for which a withdrawal interval is to be determined;

extrapolating a withdrawal interval from (a) said prior dose, (b) said prior withdrawal time, (c) said half-life data, and (d) said tolerance concentration.

2. A method according to claim 1, wherein said prior dose and said adjusted dose are carried out under different conditions, and said extrapolating step is preceded by the step of:

normalizing the conditions of said prior dose to the conditions of said adjusted dose.

3. A method according to claim 1, wherein said extrapolating step is carried out based on the slope of the line representing the tissue depletion for said compound in said tissue at said prior dose corresponding to the slope of the line representing the virtual depletion of the $99^{th}$ percentile of the population of depleting animals for said compound in said tissue at said adjusted dose.

4. A method according to claim 1, wherein said extrapolating step is carried out based on the depletion rate constant for said compound in said tissue at said prior dose corresponding to the virtual depletion rate constant representing the virtual depletion of the $99^{th}$ percentile of the population of depleting animals for said compound in said tissue at said adjusted dose.

5. A method according to claim 1, wherein said half-life data is an empirically determined effective residue half-life.

6. A method according to claim 1, wherein said half-life data is a half-life multiplier.

7. A method according to claim 6, wherein said step of extrapolating a withdrawal interval is carried out by:

determining a residue half life from said first withdrawal time and said predetermined half-life multiplier;

determining a concentration at time zero for said first dose from said tolerance concentration and said predetermined half-life multiplier;

determining a concentration at time zero for said second dose from said first dose, said second dose, and said concentration at time zero for said first dose; and then calculating said withdrawal interval from (a) said residue half-life, (b) said concentration at time zero for said second dose, and (c) said tolerance concentration.

8. A method according to claim 7, wherein said calculating step comprises executing the formula:

$$WDI = ERH \times Ln(C^{**}/TOL) \times 1.44$$

wherein:

WDI=withdrawal interval;
ERH=effective residue half-life;
$C^{**}$=concentration at time zero for said second dose; and
TOL=tolerance concentration.

9. A method according to claim 8, wherein said half-life multiplier is 5.

10. A method according to claim 1, wherein said tolerance concentration is an approved tolerance.

11. A method according to claim 1, wherein said compound is monitored in said tissue by monitoring a marker residue, and wherein tolerance concentration is a provisional acceptable tolerance determined by the method comprising:

providing an acceptable daily intake for said compound;

partitioning said acceptable daily intake among tissues according to a set of partitioning instructions;

deriving said provisional acceptable residue for said tissue of interest from said partitioned acceptable daily intake; and determining a provisional acceptable tolerance from said provisional acceptable residue.

12. A method according to claim 1, further comprising the step of:

confirming said withdrawal interval with field or regulatory data.

13. A data processing system for estimating a withdrawal interval for an adjusted dose of a compound from a prior withdrawal time for a corresponding prior dose of said compound, corresponding half-life data and a tolerance concentration, for a tissue of interest, said data processing system comprising:

means for accepting selection of an adjusted dose for said compound for which a withdrawal interval is to be determined;

means for extrapolating a withdrawal interval from (a) said prior dose, (b) said prior withdrawal time, (c) said half-life data, and (d) said tolerance concentration.

14. A system according to claim 13, wherein said prior dose and said adjusted dose are carried out under different conditions, said system further comprising:

means for normalizing the conditions of said prior dose to the conditions of said adjusted dose.

15. A system according to claim 13, wherein said means for extrapolating is based on the slope of the line representing the tissue depletion for said compound in said tissue at said prior dose corresponding to the slope of the line representing the virtual depletion of the $99^{th}$ percentile of the population of depleting animals for said compound in said tissue at said adjusted dose.

16. A system according to claim 13, wherein said means for extrapolating is based on the depletion rate constant for said compound in said tissue at said prior dose corresponding to the virtual depletion rate constant representing the virtual depletion of the $99^{th}$ percentile of the population of depleting animals for said compound in said tissue at said adjusted dose.

17. A system according to claim 13, wherein said half-life data is a half-life multiplier, and wherein said means for extrapolating includes:
 means for determining a residue half life from said first withdrawal time and said predetermined half -life multiplier;
 means for determining a concentration at time zero for said first dose from said tolerance concentration and said predetermined half-life multiplier;
 means for determining a concentration at time zero for said second dose from said first dose, said second dose, and said concentration at time zero for said first dose; and
 means for calculating said withdrawal interval from (a) said residue half-life, (b) said concentration at time zero for said second dose, and (c) said tolerance concentration.

18. A system according to claim 17, wherein said means for calculating executes the formula:

$$WDI=ERH \times Ln(C^{**}/TOL) \times 1.44$$

wherein:
 WDI=withdrawal interval;
 ERH=effective residue half-life;
 $C^{**}$=concentration at time zero for said second dose; and
 TOL=tolerance concentration.

19. A system according to claim 18, wherein said half-life multiplier is 5.

20. A system according to claim 13, wherein said tolerance concentration is an approved tolerance.

21. A system according to claim 13, wherein said compound is monitored in said tissue by monitoring a marker residue, wherein tolerance concentration is a provisional acceptable tolerance, and said system further comprises:
 means for accepting selection of an acceptable daily intake for said compound;
 means for partitioning said acceptable daily intake among tissues according to a set of partitioning instructions;
 means for deriving said provisional acceptable residue for said tissue of interest from said partitioned acceptable daily intake; and
 means for determining a provisional acceptable tolerance from said provisional acceptable residue.

22. A system according to claim 13, further comprising:
 means for confirming said withdrawal interval with field or regulatory data.

23. A method of estimating a withdrawal interval for an adjusted dose of a compound from a prior withdrawal time for a corresponding prior dose of said compound, corresponding prior half-life data and a tolerance concentration, for a tissue of interest, said method comprising the following steps that are performed in a data processing system:
 accepting selection of an adjusted dose for said compound for which a withdrawal interval is to be determined;
 extrapolating a withdrawal interval from (a) said prior dose, (b) said prior withdrawal time, (c) said half-life data, and (d) said tolerance concentration;
 wherein said half-life data is an empirically determined effective residue half-life;
 and wherein said step of extrapolating a withdrawal interval is carried out by:
 determining a half-life multiplier from said first withdrawal time and said residue half-life;
 determining a concentration at time zero for said first dose from said tolerance concentration and said half-life multiplier;
 determining a concentration at time zero for said second dose from said first dose, said second dose, and said concentration at time zero for said first dose; and then
 calculating said withdrawal interval from (a) said residue half-life, (b) said concentration at time zero for said second dose, and (c) said tolerance concentration.

24. A method according to claim 23, wherein said calculating step comprises executing the formula:

$$WDI=ERH \times Ln(C^{**}/TOL) \times 1.44$$

wherein:
 WDI=withdrawal interval;
 ERH=effective residue half-life;
 $C^{**}$=concentration at time zero for said second dose; and
 TOL=tolerance concentration.

25. A method of estimating a withdrawal interval for an adjusted dose of a compound from a prior withdrawal time for a corresponding prior dose of said compound, corresponding prior half-life data and a tolerance concentration, for a tissue of interest, said method comprising the following steps that are performed in a data processing system:
 accepting selection of an adjusted dose for said compound for which a withdrawal interval is to be determined;
 extrapolating a withdrawal interval from (a) said prior dose, (b) said prior withdrawal time, (c) said half-life data, and (d) said tolerance concentration;
 wherein said tolerance concentration is a provisional acceptable residue determined by the method comprising:
 providing an acceptable daily intake for said compound;
 partitioning said acceptable daily intake among tissues according to a set of partitioning instructions; and
 deriving said provisional acceptable residue for said tissue of interest from said partitioned acceptable daily intake.

26. A method of estimating a withdrawal interval for an adjusted dose of a compound from a prior withdrawal time for a corresponding prior dose of said compound, corresponding prior half-life data and a tolerance concentration, for a tissue of interest, said method comprising the following steps that are performed in a data processing system:
 accepting selection of an adjusted dose for said compound for which a withdrawal interval is to be determined;
 extrapolating a withdrawal interval from (a) said prior dose, (b) said prior withdrawal time, (c) said half-life data, and (d) said tolerance concentration;
 wherein said adjusted dose is modified from said prior dose for species differences, disease differences or both.

27. A method according to claim 26, wherein said adjusted dose is modified for disease differences selected from the group consisting of a change in clearance, a change in volume of distribution, and combinations thereof.

28. A method according to claim 26, wherein said adjusted dose is modified for species differences with allometric data.

29. A data processing system for estimating a withdrawal interval for an adjusted dose of a compound from a prior withdrawal time for a corresponding prior dose of said compound, corresponding half-life data and a tolerance concentration, for a tissue of interest, said data processing system comprising:

means for accepting selection of an adjusted dose for said compound for which a withdrawal interval is to be determined;

means for extrapolating a withdrawal interval from (a) said prior dose, (b) said prior withdrawal time, (c) said half-life data, and (d) said tolerance concentration;

wherein said half-life data is an empirically determined effective residue half-life, and wherein said means for extrapolating includes:

means for determining a half-life multiplier from said first withdrawal time and said residue half-life;

means for determining a concentration at time zero for said first dose from said tolerance concentration and said half-life multiplier; means for determining a concentration at time zero for said second dose from said first dose, said second dose, and said concentration at time zero for said first dose; and means for calculating said withdrawal interval from (a) said residue half-life, (b) said concentration at time zero for said second dose, and (c) said tolerance concentration.

30. A system according to claim 29, wherein said means for calculating executes the formula:

$$WDI = ERH \times Ln(C^{**}/TOL) \times 1.44$$

wherein:

WDI=withdrawal interval;

ERH=effective residue half-life;

$C^{**}$=concentration at time zero for said second dose; and

TOL=tolerance concentration.

31. A data processing system for estimating a withdrawal interval for an adjusted dose of a compound from a prior withdrawal time for a corresponding prior dose of said compound, corresponding half-life data and a tolerance concentration, for a tissue of interest, said data processing system comprising:

means for accepting selection of an adjusted dose for said compound for which a withdrawal interval is to be determined;

means for extrapolating a withdrawal interval from (a) said prior dose, (b) said prior withdrawal time, (c) said half-life data, and (d) said tolerance concentration;

wherein said tolerance concentration is a provisional acceptable residue and said system further comprises:

means for accepting selection of an acceptable daily intake for said compound;

means for partitioning said acceptable daily intake among tissues according to a set of partitioning instructions; and means for deriving said provisional acceptable residue for said tissue of interest from said partitioned acceptable daily intake.

32. A data processing system for estimating a withdrawal interval for an adjusted dose of a compound from a prior withdrawal time for a corresponding prior dose of said compound, corresponding half-life data and a tolerance concentration, for a tissue of interest, said data processing system comprising:

means for accepting selection of an adjusted dose for said compound for which a withdrawal interval is to be determined;

means for extrapolating a withdrawal interval from (a) said prior dose, (b) said prior withdrawal time, (c) said half-life data, and (d) said tolerance concentration;

further comprising means for modifying said adjusted dose from said prior dose for species differences, disease differences or both.

33. A system according to claim 32, wherein said adjusted dose is modified for disease differences selected from the group consisting of a change in clearance, a change in volume of distribution, and combinations thereof.

34. A system according to claim 32, wherein said adjusted dose is modified for species differences with allometric data.

* * * * *